US011718600B2

(12) United States Patent
Huryn et al.

(10) Patent No.: US 11,718,600 B2
(45) Date of Patent: Aug. 8, 2023

(54) 1,2,3-TRIAZOLE INHIBITORS OF P97 AAA ATPASE ACTIVITY

(71) Applicant: University of Pittsburgh—Of the Commonwealth System of Higher Education, Pittsburgh, PA (US)

(72) Inventors: Donna M. Huryn, Allentown, PA (US); Peter Wipf, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 235 days.

(21) Appl. No.: 17/046,255

(22) PCT Filed: Apr. 11, 2019

(86) PCT No.: PCT/US2019/026888
§ 371 (c)(1),
(2) Date: Oct. 8, 2020

(87) PCT Pub. No.: WO2019/200032
PCT Pub. Date: Oct. 17, 2019

(65) Prior Publication Data
US 2021/0032221 A1 Feb. 4, 2021

Related U.S. Application Data

(60) Provisional application No. 62/656,134, filed on Apr. 11, 2018.

(51) Int. Cl.
*C07D 401/14* (2006.01)
(52) U.S. Cl.
CPC ........ *C07D 401/14* (2013.01); *C07B 2200/05* (2013.01)
(58) Field of Classification Search
CPC .......................... C07D 401/14; C07B 2200/05
See application file for complete search history.

(56) References Cited

U.S. PATENT DOCUMENTS

| 5,329,102 A | 7/1994 | Sanson |
| 7,767,881 B2 | 8/2010 | Kotani et al. |
| 11,214,560 B2 | 1/2022 | Huryn et al. |
| 2005/0288347 A1 | 12/2005 | Hodge et al. |

FOREIGN PATENT DOCUMENTS

| WO | WO 2005/039569 A1 | 5/2005 |
| WO | WO 2006/130160 A2 | 12/2006 |
| WO | WO 2012/174164 A2 | 12/2012 |
| WO | WO 2017/070320 A1 | 4/2017 |
| WO | WO 2017/197080 A1 | 11/2017 |

OTHER PUBLICATIONS

Mark Rolfe et. al., The p97 Inhibitor CB-5083 is a Unique Disrupter of Protein Homeostasis in Models of Multiple Myeloma, 2017, Molecular Cancer Therapeutics, 16 (11), 2375-2386 (Year: 2017).*
David Wustrow et. al., Discovery of a First-in-Class, Potent, Selective, and Orally Bioavailable Inhibitor of the p97 AAA ATPase (CB-5083), 2015, Journal of Medicinal Chemistry, 58, 9480-9497 (Year: 2015).*
Jose Luiz Pedroso et. al., One Family, one gene and three phenotypes: a novel VCP (valosin-containing protein) mutation associated with myopathy with rimmed vacuoles, amyotrophic lateral sclerosis and frontotemporal dementia, 2016, Journal of the Neurological Sciences, 368, 352-358 (Year: 2016).*
Hiroyuki Zhimizu et. al., Valosin-Containing Protein (VCP/p97) Is Required for Poliovirus Replication and is Involved in Cellular Protein Secretion Pathway in Poliovirus Infection, 2012, Journal of Virology, 5541-5553 (Year: 2012).*
Finn Grey et. al., The host ubiquitin-dependent segregase VCP/p97 is required for the onset of human cytomegalovirus replication, 2017, PLOS Pathogens, 1-23 (Year: 2017).*
Di Xia et. al., Mutations in the Human AAA+ Chaperone p97 and Related Diseases, 2016, Frontiers in Molecular Biosciences, 1-12 (Year: 2016).*
James J. La Clair et. al., Inhibitors of the AAA+ Chaperone p97, 2015, Molecules, 20, 3027-3049 (Year: 2015).*
Magnaghi et al., "Covalent and allosteric inhibitors of the ATPase VCP/p97 induce cancer cell death," Nature Chemical Biology, vol. 9, pp. 548-559 (2013).
Non-Final Office Action on U.S. Appl. No. 16/301,080 dated Apr. 22, 2020.
Non-Final Office Action on U.S. Appl. No. 16/612,342 dated Dec. 14, 2020.
Notice of Allowance on U.S. Appl. No. 16/301,080 dated Aug. 18, 2020.
International Preliminary Report on Patentability issued in International Patent Application No. PCT/US2018/032062, dated completed, Nov. 21, 2019.
International Search Report issued in International Patent Application No. PCT/US2018/032062, dated Sep. 13, 2018.
PubChem CID 70041846 Date Created Dec. 1, 2012, Dated Accessed: Aug. 27, 2018, 14 pages.
International Search Report and Written Opinion issued in related International Patent Application No. PCT/US2017/032099, dated Aug. 4, 2017.
Pubchem, CHEMBL2315453, Jun. 11, 2013, pp. 1-7 [online], [retrieved on Jul. 12, 2017], Retrieved from the internet from https://pubchem.ncbi.nlm.nih.gov/compounds/71520307#section=2D-Structure; pp. 2-3, 6.

(Continued)

*Primary Examiner* — Mark L Shibuya
*Assistant Examiner* — Luisalberto Gonzalez
(74) *Attorney, Agent, or Firm* — Foley & Lardner LLP

(57) ABSTRACT

The present technology is directed to methods of inhibiting or modulating p97 and compounds and compositions useful in such methods. Diseases and conditions that can be treated with the compounds and compositions of the present technology include, but are not limited to, antibacterial infection, antiviral infection, cancer and neurodegenerative disorders susceptible to treatment by modulation of p97.

15 Claims, No Drawings

(56) References Cited

OTHER PUBLICATIONS

Pubchem, CHEMBL2315448, Jun. 11, 2013, p. 1-7 [online], [retrieved on Jul. 12, 2017], Retrieved from the internet from https://pubchem.ncbi.nlm.nih.gov/compounds/71521795#section=BioAssay-Results; pp. 2-3.
Alverez, et al., Allosteric Indole Amide Inhibitors of p97: Identification of a Novel Probe of the Ubiquitin Pathway, ACS Medicinal Chemistry Letters, vol. 7, pp. 182-187, p. 183, figure 1 (2016).
Non-Final Office Action issued in co-pending U.S. Appl. No. 16/612,342, dated Apr. 6, 2021.
Chemical Abstracts Service CAS Registry Nos. 1028266-83-2, 1027936-59-9 and 1026710-07-05, CAplus database entry dates of Jun. 15, 2008, Jun. 13, 2008, and Jun. 9, 2008, 1 page.
Notice of Allowance issued in co-pending U.S. Appl. No. 16/612,342, dated Aug. 18, 2021.
Arpicco et al., "Anticancer prodrugs: An overview of major strategies and recent developments," Curr. Top. Med. Chem., 11: 2346-2381 (2011).
Banerjee, et al., "2.3 A resolution cryo-EM structure of human p97 and mechanism of allosteric Inhibitition," Sciencei, vol. 331, No. 6275, pp. 871-875 (2016).
Blencowe et al., "Self-immolative linkers in polymeric delivery systems," Polym. Chem., 2: 773-790 (2011); Arpicco et al., "Anticancer prodrugs: An overview of major strategies and recent developments," Curr. Tot>. Med. Chem. (Shariah, United Arab Emirates), 11: 2346-2381 (2011).
Bodor, N., "Novel Approaches in Prodrug Design," Drugs of the Future, vol. 6, pp. 165-182 (1981).
Bundgaard, H., "Design of Prodrugs: Bioreversible-Derivatives for Various Functional Groups and Chemical Entities," in Design of Prodrugs, Elsevier (1985), 1 page Abstract.
Deshaies et al., "Proteotoxic crisis, the ubiquitin-proteasome system, and cancer therapy," BMC Biology, 12(94), 14 pages (2014).
Huttunen et al., "Prodrugs—from serendipity to rational design," Pharmacol. Rev., 63, 750-771 (2011).
Franke et al., "Mutan Analysis Reveals Allosteric Regulation of ClpB Disaggregase," Frontiers in Molecular Biosciencesi, vol. 4, No. 6, 13 pages (Feb. 2017).

Karaman, R., "Prodrugs design based on inter- and intramolecular chemical processes," Chem. Biol. Drug Des., 82: 643-668 (2013).
Lee et al., "Pro-drug and Antedrug: Two Diametrical Approaches in Designing Safer Drugs," Arch. Pharm. Res., 25: 111-136 (2002).
Meyer et al., "Emerging functions of the VCP/p97 AAA-ATPase in the ubiquitin system," Nature Cell Biology, 14: 117-123 (2012).
Meyer et al., "The VCP/p97 system at a glance: connecting cellular function to disease pathogenesis," J. Cell Sci., 127, pp. 3877-3883 (2014).
Notari, "Theory and Practice of Prodrug Kinetics," Methods in Enzymology, vol. 112, pp. 309-323 (1985).
Rautio et al., "Prodrugs: Design and clinical applications," Nat. Rev. Drug Discovery, 7: 255-270 (2008).
Simplicio et al., "Prodrugs for amines," Molecules, 13: 519-547 (2008).
Tietze et al., "Antibody-directed enzyme prodrug therapy: A promising approach for a selective treatment of cancer based on prodrugs and monoclonal antibodies" Chem. Biol. Drug Des., 74: 205-211 (2009).
Valle et al., "Critical Role of VCP/p97 in the Pathogenesis and Progression of Non-Small Cell Lung Carcinoma," PlosOne, 6(12): e29073, 12 pages (2011).
Zhang et al., "Structure of the AAA ATPase p97," Molecular Cell, 6(6): 1473-1484 (2000).
Zhang, et al., "Altered cofactor regulation with disease-associated p97NCP mutations," Proc. Natl. Acad. Sci. USA, 112(14), E1705-E1714 (2015).
Burnett, et al., "A Threonine Turnstile Defines a Dynamic Amphiphilic Binding Motif in the AAA ATPase p97 Allosteric Binding Site," Org. Biomol. Chem., vol. 15, No. 19, pp. 4096-4114 (May 2017).
International Search Report and Written Opinion issued in International Patent Application No. PCT/US2019/026888, completed Jun. 5, 2019.
Polucci, et al., "Alkylsulfanyl-1,2,4-triazoles, a New Class of Allosteric Valosine Containing Protein Inhibitors. Synthesis and Structure-Activity Relationships," Journ. of Medicinal Chemistry, vol. 56, pp. 437-450 (2013).
Office Action issued in co-pending U.S. Appl. No. 17/544,863, dated Jan. 30, 2023.
U.S. Notice of Allowance Issued in co-pending U.S. Appl. No. 17/544,863 dated May 8, 2023 (9 pages).

\* cited by examiner

1,2,3-TRIAZOLE INHIBITORS OF P97 AAA ATPASE ACTIVITY

CROSS-REFERENCE TO RELATED APPLICATION

This application claims the priority benefits under 35 USC § 119 to U.S. provisional Application 62/656,134, filed Apr. 11, 2018, the entire contents of which are incorporated herein by reference in their entirety.

STATEMENT OF GOVERNMENT SUPPORT

This application is the U.S. National Stage of International Patent Application No. PCT/US2019/026888, filed Apr. 11, 2019, which claims priority from U.S. Provisional Patent Application No. 62/656,134, filed Apr. 11, 2018, the entire contents of these applications are incorporated herein by reference in their entirety.

BACKGROUND

The AAA ATPase p97 (also known as valosin-containing protein (VCP), Cdc48 in yeast and plants, CDC-48 in worms and Ter94 in flies), is a member of the AAA family (ATPases associated with diverse cellular activities). Zhang et al., "Structure of the AAA ATPase p97," *Mol. Cell*, 6(6): 1473-84 (2000).

Recent studies have uncovered cellular functions for p97 in autophagy, endosomal sorting and regulation of protein degradation at the outer mitochondrial membrane, and elucidated a role for p97 in key chromatin-associated processes. These findings extend the functional relevance of p97 to lysosomal degradation and reveal a dual role in protecting cells from protein stress and ensuring genome stability during proliferation. Meyer et al., "Emerging functions of the VCP/p97 AAA-ATPase in the ubiquitin system," *Nature Cell Biol.*, 14: 117-123 (2012).

p97 also functions as an interaction hub, and different sets of at least 30 cofactors have been shown to be responsible for modulating p97-mediated processes. Meyer et al., "The VCP/p97 system at a glance: connecting cellular function to disease pathogenesis," *J. Cell Sci.*, 127: 1-7 (2014).

A 2.3 Å resolution cryo-EM structure of human p97 and mechanism of allosteric inhibition was recently disclosed. Banerjee et al., *Science*, 351(6275): 871-875 (2016). Previously, other structures have also been disclosed, see, e.g., Wipf et al., *Organic & Biomolecular Chemistry* (2017), DO:10.1039/C7OB00526A.

p97-associated disease: p97 is a potential therapeutic target for cancer and neurodegenerative diseases. Given the crucial role of p97 in maintaining cellular proteostasis, it is not surprising that autosomal dominant mutations in p97, the gene encoding p97, lead to a rare multisystem degenerative disorder previously termed IBMPFD/ALS. The acronym IBMPFD/ALS refers to the four main phenotypes that can affect patients carrying disease-associated mutations of p97 (i.e., inclusion body myopathy (IBM), Paget's disease of the bone (PDB), frontotemporal dementia (FTD) and amyotrophic lateral sclerosis (ALS)). However, a patient with a pathogenic p97 mutation can have any mixture of phenotypes, including all four phenotypes or just one phenotype in isolation. In addition, a member of the same family can have any combination of phenotypes. Id.

Some carriers of p97 mutation also manifest additional symptoms, including Parkinsonism, ataxia, cataracts, dilated cardiomyopathy, hepatic fibrosis, and hearing loss. The term 'multisystem proteinopathy' has been proposed as the nomenclature for an emerging family of genetic disorders that are unified by this characteristic variation in the penetrance of muscle, bone and CNS degenerative phenotypes along with the accumulation of ubiquitin and TDP-43-positive inclusions.

The protein p97 plays an important role in protein homeostasis. However, in numerous disease states, homeostasis is dysregulated, and inhibitors and/or modulators of p97 have the potential to address diseases such as cancer, and neurodegenerative disorders. The compounds described inhibit the ATPase activity of p97, have effects on p97-dependent mechanisms in cells and exhibit anti-proliferative activity. They have the potential to be anti-cancer agents, or drugs that are effective in neurodegenerative diseases, or any other disorder that relies on p97. Inhibitors of homologous proteins in bacteria and/or viruses could also be useful to treat infectious diseases. Inhibitors of AAA ATPases may also be useful to treat antibacterial and/or antiviral infections (see, e.g., (1) Cold Spring Harbor Perspect. Med. (2015); 5:a021154; and (2) Franke et al., "Mutant Analysis Reveals Allosteric Regulation of Clpb Disaggregase." *Front. Mol. Biosci.*, 4: 6 (2017)).

There remains a need in the art for inhibitors and/or modulators of p97 useful in treating cancer and neurodegenerative disorders caused by proteostatic malfunctions. Further, there remains a need for compounds that are more efficacious with fewer side effects than other compounds that work through similar or unrelated p97 inhibition mechanisms. The present technology satisfies these needs.

SUMMARY OF THE DISCLOSED SUBJECT MATTER

The present technology is directed to methods of modulating p97 or inhibiting p97, and compounds and compositions useful in such methods. Diseases and conditions that can be treated with the compounds and compositions of the technology include, but are not limited to, antibacterial and/or antiviral infections, cancer, and neurodegenerative disorders susceptible to treatment by modulation or inhibition of p97. Exemplary neurodegenerative disorders include, but are not limited to, inclusion body myopathy (IBM), Paget's disease of the bone (PDB), frontotemporal dementia (FTD), and amyotrophic lateral sclerosis (ALS).

Subjects having p97 mutations may also be treated with the compounds and compositions according to the present technology. Such p97 mutations may manifest symptoms including but not limited to Parkinsonism, ataxia, cataracts, dilated cardiomyopathy, hepatic fibrosis, and hearing loss. Treatment with a compound or composition according to the present technology may eliminate or ameliorate such symptoms.

In one aspect, provided is a compound having a structure of Formula (Ia):

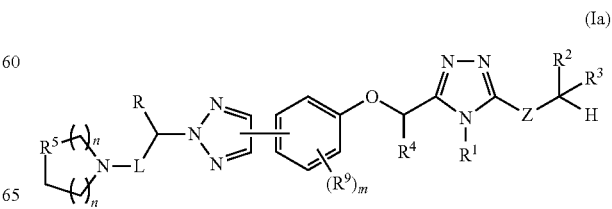

or a stereoisomer thereof, or a pharmaceutically acceptable salt, solvate or prodrug thereof, wherein:

Z is O, $SO_{0-2}$, NR, or $C(R^7)_2$;

L is C(O) or $SO_{1-2}$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

m is 0, 1, 2, 3, or 4;

each n is independently 0, 1, 2, 3, or 4;

$R^5$ is $C(R^6)_2$, NR', $SO_{0-2}$, or O;

R is independently selected from the group consisting of H, optionally substituted alkyl, and optionally substituted cycloalkyl;

$R^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —$N(R')_2$; —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic);

$R^7$ is independently selected from the group consisting of H, halogen, optionally substituted alkyl, optionally substituted cycloalkyl, —OR, and —$N(R)_2$;

$R^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic); or two $R^8$, together with the nitrogen atom to which they are attached, form an optionally substituted heterocyclic ring; and $R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$.

In another aspect, provided is a compound having a structure of Formula (Ib):

(Ib)

or a stereoisomer thereof, or a pharmaceutically acceptable salt, solvate or prodrug thereof, wherein:

Z is O, $SO_{0-2}$, NR, or $C(R^7)_2$;

L is C(O) or $SO_{0-2}$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

m is 0, 1, 2, 3, or 4;

each n is independently 0, 1, 2, 3, or 4;

$R^5$ is $C(R^6)_2$, NR', $SO_{0-2}$, or O;

R is independently selected from the group consisting of H, optionally substituted alkyl, and optionally substituted cycloalkyl;

$R^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —$N(R')_2$; —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substi- $R^7$ is independently selected from the group consisting of H, halogen, optionally substituted alkyl, optionally substituted cycloalkyl, —OR, and —$N(R)_2$;

$R^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic); or two $R^8$, together with the nitrogen atom to which they are attached, form an optionally substituted heterocyclic ring; and $R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$.

In some embodiments of a compound of Formula (Ia) or (Ib), $R^9$ is halogen, nitrile, a $C_1$-$C_6$ alkyl, or O—$C_1$-$C_6$ alkyl. In some embodiments of a compound of Formula (Ia) or (Ib), $R^5$ is NR'. In some embodiments of a compound of Formula (Ia) or (Ib), $R^5$ is $C(R^6)_2$. In some embodiments of a compound of Formula (Ia) or (Ib), n is 1. In some embodiments of a compound of Formula (Ia) or (Ib), $R^1$ is pyridine. In some embodiments of a compound of Formula (Ia) or (Ib), $R^2$ and $R^3$ together are a cyclopropyl, cyclopentyl, cyclohexene, or a perdeuterated cycloalkyl ring. In some embodiments of a compound of Formula (Ia) or (Ib), Z is S. In some embodiments of a compound of Formula (Ia) or (Ib), $R^4$ is H.

In another aspect, provided is a compound having a structure of Formula (IIa):

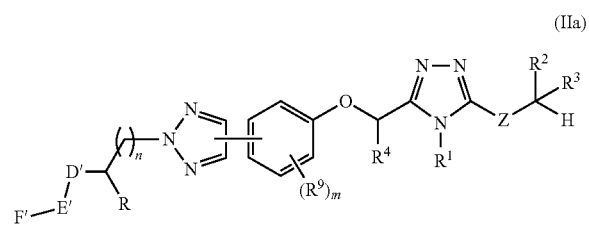

(IIa)

or a stereoisomer thereof, or a pharmaceutically acceptable salt, solvate or prodrug thereof, wherein:

Z is O, $SO_{0-2}$, NR, or $C(R^7)_2$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

R is independently selected from the group consisting of H, optionally substituted alkyl, and optionally substituted cycloalkyl;

$R^7$ is independently selected from the group consisting of H, halogen, optionally substituted alkyl, optionally substituted cycloalkyl, —OR, and —$N(R)_2$;

m is 0, 1, 2, 3, or 4;

n is 1, 2, 3, or 4;

$R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$;

D' is selected from the group consisting of a bond, optionally substituted alkyl, —O—, —S—, —NR—, —$NRSO_2$—, —$SO_2NR$—, —C(O)—, —C(O)O—, —C(O)NR—, —OC(O)—, —OC(O)NR—, —$NRSO_2$—, —NRC(O)—, —$NRSO_2NR$—, —NRC(O)O—, —NRCONR—, and —NRC(NR)NR—;

E' is selected from the group consisting of a bond, an optionally substituted $C_1$-$C_6$ alkyl, optionally substituted $C_2$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl.

In another aspect, provided is a compound having a structure of Formula (IIb):

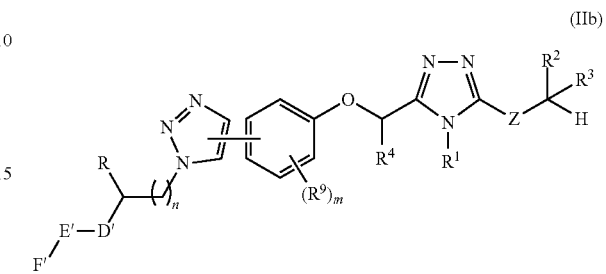

(IIb)

or a stereoisomer thereof, or a pharmaceutically acceptable salt, solvate or prodrug thereof, wherein:

Z is O, $SO_{0-2}$, NR, or $C(R^7)_2$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

R is independently selected from the group consisting of H, optionally substituted alkyl, and optionally substituted cycloalkyl;

$R^7$ is independently selected from the group consisting of H, halogen, optionally substituted alkyl, optionally substituted cycloalkyl, —OR, and —$N(R)_2$;

m is 0, 1, 2, 3, or 4;

n is 1, 2, 3, or 4;

$R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$;

D' is selected from the group consisting of a bond, optionally substituted alkyl, —O—, —S—, —NR—, —$NRSO_2$—, —$SO_2NR$—, —C(O)—, —C(O)O—, —C(O)NR—, —OC(O)—, —OC(O)NR—, —$NRSO_2$—, —NRC(O)—, —$NRSO_2NR$—, —NRC(O)O—, —NRCONR—, and —NRC(NR)NR—;

E' is selected from the group consisting of a bond, an optionally substituted $C_1$-$C_6$ alkyl, optionally substituted $C_2$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl.

In some embodiments of a compound of Formula (IIa) or (IIb), $R^9$ is halogen, nitrile, a $C_1$-$C_6$ alkyl, or O—$C_1$-$C_6$ alkyl. In some embodiments of a compound of Formula (IIa) or (IIb), n is 1. In some embodiments of a compound of Formula (IIa) or (IIb), $R^1$ is pyridine. In some embodiments of a compound of Formula (IIa) or (IIb), $R^2$ and $R^3$ together are a cyclopropyl, cyclopentyl, cyclohexene, or a perdeuterated cycloalkyl ring. In some embodiments of a compound of Formula (IIa) or (IIb), Z is S. In some embodiments of a compound of Formula (IIa) or (Ib), $R^4$ is H.

Some embodiments include a compound selected from those depicted in Table I, or a stereoisomer, or a pharmaceutically acceptable salt, solvate or prodrug thereof.

Some embodiments include a pharmaceutical composition comprising a compound of any of the embodiments herein and at least one pharmaceutically acceptable excipient.

In another aspect, provided is a method of inhibiting p97 in a subject in need thereof, comprising administering to the subject a therapeutically effective amount of a compound of any one of the embodiments herein or a therapeutically effective amount of a pharmaceutical composition comprising a compound of any one of the embodiments herein.

In another aspect, provided is a method of modulating p97 in a subject in need thereof, comprising administering to the subject a therapeutically effective amount of a compound of any one of the embodiments herein or a therapeutically effective amount of a pharmaceutical composition comprising a compound of any one of the embodiments herein.

In another aspect, provided is a method of treating cancer or a neurodegenerative disease susceptible to treatment by p97 inhibition in a subject in need thereof comprising administering to the subject a therapeutically effective amount of a compound of any of the embodiments herein or a therapeutically effective amount of a pharmaceutical composition comprising a compound of any one of the embodiments herein. In some embodiments, the method is a method of treating cancer susceptible to treatment by p97 inhibition, wherein the cancer is selected from the group consisting of a solid tumor, non-small cell lung carcinoma, multiple myeloma, colon cancer, and mantle cell lymphoma. In some embodiments, the method is a method of treating a neurodegenerative disease susceptible to treatment by p97 inhibition, wherein the neurodegenerative disease is selected from the group consisting of inclusion body myopathy (IBM), Paget's disease of the bone (PDB), frontotemporal dementia (FTD), and amyotrophic lateral sclerosis (ALS).

In another aspect, provided is a method of treating antibacterial and/or antiviral infection in a subject in need thereof comprising administering to the subject a therapeutically effective amount of a compound of any of the embodiments herein or a therapeutically effective amount of a pharmaceutical composition comprising a compound of any one of the embodiments herein.

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction. Additional embodiments may be disclosed in the Detailed Description below.

DETAILED DESCRIPTION

I. Compounds of the Disclosure

The present disclosure provides triazoles with p97 inhibitory activity or p97 modulatory activity.

In some embodiments, compounds of the present disclosure include those represented by Formula (Ia):

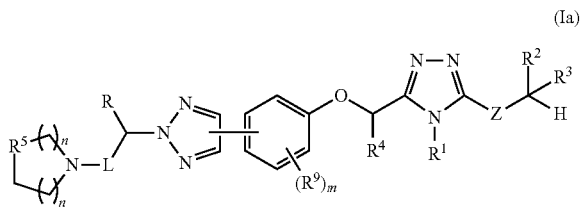

(Ia)

or a stereoisomer thereof, or a pharmaceutically acceptable salt, solvate or prodrug thereof, wherein:

Z is O, $SO_{0-2}$, NR, or $C(R^7)_2$;

L is C(O) or $SO_{1-2}$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

m is 0, 1, 2, 3, or 4;

each n is independently 0, 1, 2, 3, or 4;

$R^5$ is $C(R^6)_2$, NR', $SO_{0-2}$, or O;

R is independently selected from the group consisting of H, optionally substituted alkyl, and optionally substituted cycloalkyl;

$R^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —N(R')$_2$; —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic);

$R^7$ is independently selected from the group consisting of H, halogen, optionally substituted alkyl, optionally substituted cycloalkyl, —OR, and —N(R)$_2$;

$R^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic); or two $R^8$, together with the nitrogen atom to which they are attached, form an optionally substituted heterocyclic ring; and R⁹ is independently selected from the group consisting of halogen, nitrile, optionally substituted alkyl, optionally substituted cycloalkyl, —NR₂, —SF₅, —OR, —CO₂R, —SR, —SOR, and —SO₂R.

In some embodiments, compounds of the present disclosure include those represented by Formula (Ib):

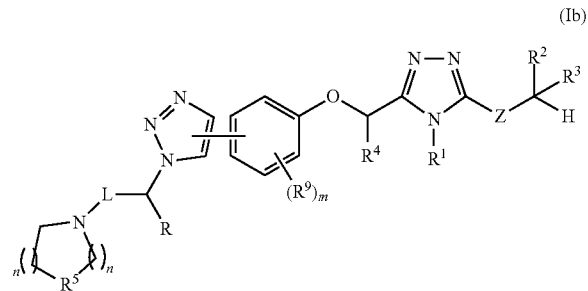

(Ib)

or a stereoisomer thereof, or a pharmaceutically acceptable salt, solvate or prodrug thereof, wherein:

Z is O, SO₀₋₂, NR, C(R⁷)₂;

L is C(O) or SO₀₋₂;

R² and R³ are independently an optionally substituted C₁₋₉ cyclic, C₃₋₉ heterocyclic, or halogen, or R² and R³ together form an optionally substituted C₃₋₉ cyclic or 3- to 9-membered heterocyclic ring;

R¹ is optionally substituted phenyl, optionally substituted 5- or 6-membered heteroaryl, or optionally substituted non-aromatic heterocyclic;

R⁴ is H, C(R⁷)₃, aryl, or heteroaryl;

m is 0, 1, 2, 3, or 4;

each n is independently 0, 1, 2, 3, or 4;

R⁵ is C(R⁶)₂, NR', SO₀₋₂, or O;

R is independently selected from the group consisting of H, optionally substituted alkyl, and optionally substituted cycloalkyl;

R⁶ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —N(R')₂; —C(O)-(optionally substituted alkyl); —C(O)O-(optionally substituted alkyl); —C(O)(NR)-(optionally substituted alkyl); —SO₀₋₂-(optionally substituted alkyl); —C(O)-(optionally substituted cycloalkyl); —C(O)O-(optionally substituted cycloalkyl); —C(O)(NR)-(optionally substituted cycloalkyl); —SO₀₋₂-(optionally substituted cycloalkyl); —C(O)-(optionally substituted aryl); —C(O)O-(optionally substituted aryl); —C(O)(NR)-(optionally substituted aryl); —SO₀₋₂-(optionally substituted aryl); —C(O)-(optionally substituted heterocyclic); —C(O)O-(optionally substituted heterocyclic); —C(O)(NR)-(optionally substituted heterocyclic); and —SO₀₋₂-(optionally substituted heterocyclic);

R⁷ is independently selected from the group consisting of H, halogen, optionally substituted alkyl, optionally substituted cycloalkyl, —OR, and —N(R)₂;

R⁸ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —SO₀₋₂-(optionally substituted alkyl); —C(O)-(optionally substituted cycloalkyl); —C(O)O-(optionally substituted cycloalkyl); —C(O)(NR)-(optionally substituted cycloalkyl); —SO₀₋₂-(optionally substituted cycloalkyl); —C(O)-(optionally substituted aryl); —C(O)O-(optionally substituted aryl); —C(O)(NR)-(optionally substituted aryl); —SO₀₋₂-(optionally substituted aryl); —C(O)-(optionally substituted heterocyclic); —C(O)O-(optionally substituted heterocyclic); —C(O)(NR)-(optionally substituted heterocyclic); and —SO₀₋₂-(optionally substituted heterocyclic); or two R⁸, together with the nitrogen atom to which they are attached, form an optionally substituted heterocyclic ring; and R⁹ is independently selected from the group consisting of halogen, nitrile, optionally substituted alkyl, optionally substituted cycloalkyl, —NR₂, —SF₅, —OR, —CO₂R, —SR, —SOR, and —SO₂R.

In some embodiments, compounds of the present disclosure include those represented by Formula (IIa):

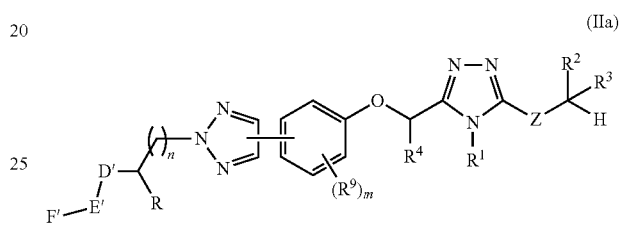

(IIa)

or a stereoisomer thereof, or a pharmaceutically acceptable salt, solvate or prodrug thereof, wherein:

Z is O, SO₀₋₂, NR, or C(R⁷)₂;

R² and R³ are independently an optionally substituted C₁₋₉ cyclic, C₃₋₉ heterocyclic, or halogen, or R² and R³ together form an optionally substituted C₃₋₉ cyclic or 3- to 9-membered heterocyclic ring;

R¹ is optionally substituted phenyl, optionally substituted 5- or 6-membered heteroaryl, or optionally substituted non-aromatic heterocyclic;

R⁴ is H, C(R⁷)₃, aryl, or heteroaryl;

R is independently selected from the group consisting of H, optionally substituted alkyl, and optionally substituted cycloalkyl;

R⁷ is independently selected from the group consisting of H, halogen, optionally substituted alkyl, optionally substituted cycloalkyl, —OR, and —N(R)₂;

m is 0, 1, 2, 3, or 4;

n is 1, 2, 3, or 4;

R⁹ is independently selected from the group consisting of halogen, nitrile, optionally substituted alkyl, optionally substituted cycloalkyl, —NR₂, —SF₅, —OR, —CO₂R, —SR, —SOR, and —SO₂R;

D' is selected from the group consisting of a bond, optionally substituted alkyl, —O—, —S—, —NR—, —NRSO₂—, —SO₂NR—, —C(O)—, —C(O)O—, —C(O)NR—, —OC(O)—, —OC(O)NR—, —NRSO₂—, —NRC(O)—, —NRSO₂NR—, —NRC(O)O—, —NRCONR—, and —NRC(NR)NR—;

E' is selected from the group consisting of a bond, an optionally substituted C₁-C₆ alkyl, optionally substituted C₁-C₆ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl.

In some embodiments, compounds of the present disclosure include those represented by Formula (IIb):

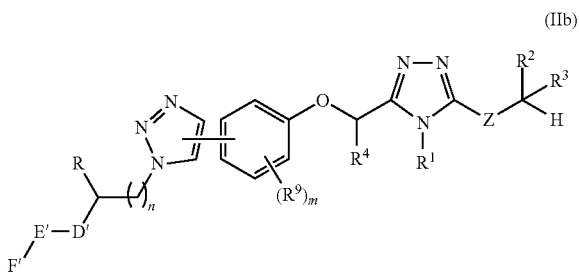

(IIb)

or a stereoisomer thereof, or a pharmaceutically acceptable salt, solvate or prodrug thereof, wherein:

Z is O, $SO_{0-2}$, NR, or $C(R)_2$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

R is independently selected from the group consisting of H, optionally substituted alkyl, and optionally substituted cycloalkyl;

$R^7$ is independently selected from the group consisting of H, halogen, optionally substituted alkyl, optionally substituted cycloalkyl, —OR, and —N(R)$_2$;

m is 0, 1, 2, 3, or 4;

n is 1, 2, 3, or 4;

$R^9$ is independently selected from the group consisting of halogen, nitrile, optionally substituted alkyl, optionally substituted cycloalkyl, —NR$_2$, —SF$_5$, —OR, —CO$_2$R, —SR, —SOR, and —SO$_2$R;

D' is selected from the group consisting of a bond, optionally substituted alkyl, —O—, —S—, —NR—, —NRSO$_2$—, —SO$_2$NR—, —C(O)—, —C(O)O—, —C(O)NR—, —OC(O)—, —OC(O)NR—, —NRSO$_2$—, —NRC(O)—, —NRSO$_2$NR—, —NRC(O)O—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl.

In some embodiments of a compound of Formulae (Ia) or (IIa), the 1,2,3-triazole is connected to the adjacent phenyl ring as shown in the structure:

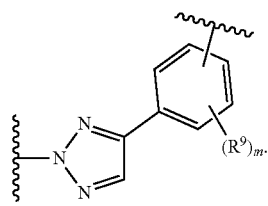

In some embodiments of a compound of Formulae (Ib) or (Ib), the 1,2,3-triazole is connected to the adjacent phenyl ring as shown in the structure:

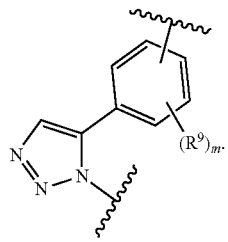

In some embodiments of a compound of Formulae (Ib) or (Ib), the 1,2,3-triazole is connected to the adjacent phenyl ring as shown in the structure:

In some embodiments of a compound of Formulae (Ia), (Ib), (IIa), or (IIb), Z is selected from the group consisting of O, S, and $C(R^7)_2$, where $R^7$ is independently H, halogen, optionally substituted $C_1$-$C_6$ alkyl, optionally substituted $C_3$-$C_{10}$ cycloalkyl, or —N(R)$_2$. In some embodiments, R or $R^7$ is H. In some embodiments, $R^7$ is H. In some embodiments, Z is CH$_2$. In some embodiments, Z is O. In some embodiments, Z is S. In some embodiments, Z is selected from the group consisting of O, S and CH$_2$.

In some embodiments of a compound of Formulae (Ia) or (Ib), $R^5$ is $C(R^6)_2$, NR$^8$, SO$_{0-2}$, or O. In some embodiments, $R^5$ is $C(R^6)_2$. In some embodiments, $R^5$ is CH(R$^6$). In some embodiments, $R^5$ is NR'. In some embodiments, $R^5$ is SO$_{0-2}$. In some embodiments, $R^5$ is O.

In some embodiments of a compound of Formulae (Ia) or (Ib), each n is selected such that the heterocyclic ring is a 3- to 9-membered ring. In some embodiments, each n is selected such that the heterocyclic ring is a 4- to 7-membered ring. In some embodiments, each n is selected such that the heterocyclic ring is an optionally substituted aziridine, optionally substituted azetidine, optionally substituted pyrrolidine, optionally substituted piperidine, optionally substituted piperazine, morpholine, thiomorpholine, optionally substituted homopiperazine, optionally substituted azepane, or optionally substituted azocane. In some embodiments, each n is selected such that the heterocyclic ring is optionally substituted pyrrolidine, optionally substituted piperidine, optionally substituted piperazine, morpholine, or thiomorpholine. In some embodiments, each n is selected such that the heterocyclic ring is optionally substituted piperazine.

In some embodiments of a compound of Formulae (IIa) or (IIb), n is 1. In some embodiments, n is 2. In some embodiments, n is 3. In some embodiments, n is 4.

In some embodiments of a compound of Formulae (IIa) or (IIb), D' is selected from the group consisting of —O—, —NH—, —C(O)—, —C(O)O—, —OC(O)NH—, —OC(O)—, —NHSO$_2$—, —NHCO—, —NHSO$_2$NH—, —NHCOO—, and —NHCONH—. In some embodiments, D' is —O—, —NH—, —C(O)—, —C(O)O—, —OC(O)

NH—, —OC(O)—, —NHCO—, or —NHCOO—. In some embodiments, D' is —O—. In some embodiments, D' is —NH—. In some embodiments, D' is —OC(O)NH—. In some embodiments, D' is —OC(O)—. In some embodiments, D' is —C(O)O—. In some embodiments, D' is —C(O)—. In some embodiments, D' is —NHCO—. In some embodiments, D' is —NHCOO—.

In some embodiments of Formulae (IIa) or (IIb), E' is a bond, an optionally substituted $C_1$-$C_6$ alkyl, optionally substituted $C_2$-$C_6$ alkenyl, or optionally substituted $C_3$-$C_{10}$ cycloalkyl. In some embodiments, E' is a bond, an optionally substituted $C_1$-$C_6$ alkyl, or optionally substituted $C_3$-$C_{10}$ cycloalkyl. In some embodiments, E' is an optionally substituted $C_1$-$C_6$ alkyl. In some embodiments, E' is an optionally substituted $C_1$-$C_6$ alkyl and F' is H. In some embodiments, E' is an optionally substituted $C_3$-$C_6$ cycloalkyl, (e.g., optionally substituted with alkyl, halogen, or —OR). In some embodiments, the cycloalkyl is specifically selected from, e.g., one of the following: cyclopropyl, cyclobutyl, cyclopentyl, and cyclohexyl, each of which may be optionally substituted. In some embodiments, E' is $C_1$-$C_6$ alkyl and F' is H.

In some embodiments of Formulae (IIa) or (IIb), F' is an optionally substituted $C_3$-$C_{10}$ cycloalkyl, an optionally substituted non-aromatic 3- to 9-membered heterocycle, an optionally substituted $C_6$ aryl, or an optionally substituted 5- or 6-membered heteroaryl, each of which is described below in further detail. In some embodiments, F' is substituted with one or more $C_1$-$C_6$ alkyl, perfluoroalkyl (e.g., $CF_3$), —OR, —CN, —$CO_2R$, halogen, —SR, —SOR, —$SO_2R$, —$SF_5$, or —$NR_2$, or any combination thereof. In some embodiments, F' is not substituted.

In some embodiments of Formulae ((IIa) or (IIb), F' is an optionally substituted cycloalkyl. For example, F' may be a $C_3$-$C_6$ cycloalkyl, optionally substituted with $C_1$-$C_6$ alkyl, halogen, or —OR. In some embodiments, the cycloalkyl is specifically selected from, e.g., one of the following: cyclopropyl, cyclobutyl, cyclopentyl, and cyclohexyl, each of which may be optionally substituted. In some embodiments, the cycloalkyl is specifically selected from, e.g., one of the following: cyclopropyl, cyclobutyl, cyclopentyl, cyclohexyl, and propellane, each of which may be optionally substituted. In some embodiments, E' is a bond and F' is an optionally substituted $C_3$-$C_{10}$ cycloalkyl. In some embodiments, E' is optionally substituted $C_1$-$C_6$ alkyl and F' is an optionally substituted $C_3$-$C_{10}$ cycloalkyl.

In some embodiments of Formulae (IIa) or (IIb), F' is an optionally substituted heterocycle. For example, F' may be a 4- to 6-membered non-aromatic heterocycle, optionally substituted with $C_1$-$C_6$ alkyl, halogen, or OR. In some embodiments, the heterocycle contains one or more heteroatom selected from: O, S, SO, $SO_2$, B, N, and NR. Particular embodiments include, e.g., morpholine, azetidine, alkyl-piperidine, alkyl-piperazine, alkyl-diazepane, thiomorpholine 1,1-dioxide, isoindoline-1,3-dione, tetrahydropyran, and pyrrolidone. In some embodiments, E' is a bond and F' is an optionally substituted non-aromatic 4- to 6-membered heterocycle. In some embodiments, E' is optionally substituted $C_1$-$C_6$ alkyl and F' is an optionally substituted non-aromatic 4- to 6-membered heterocycle.

In some embodiments of Formulae (IIa) or (IIb), F' is an optionally substituted aryl. For example, F' may be a $C_6$-$C_{10}$ aryl, e.g., a phenyl, that is optionally substituted, e.g., with one or more of $C_1$-$C_6$ alkyl, perfluoroalkyl (e.g., $CF_3$), —OR, —CN, —$CO_2R$, halogen, —SR, —SOR, —$SO_2R$, —$SF_5$, or —$NR_2$, or any combination thereof. In some embodiments, E' is a bond and F' is an optionally substituted $C_6$-$C_{10}$ aryl. In some embodiments, E' is optionally substituted $C_1$-$C_6$ alkyl and F' is an optionally substituted $C_6$-$C_{10}$ aryl.

In some embodiments of Formulae (IIa) or (IIb), F' is an optionally substituted heteroaryl. For example, F' may be a 5- or 6-membered heteroaryl, optionally substituted with $C_1$-$C_6$ alkyl, halogen, or OR. In some embodiments, the heteroaryl contains one or more heteroatom selected from O, S, SO, N, and NR. Particular embodiments include, e.g., triazole, tetrazole, imidazole, and isoxazole. In some embodiments, E' is a bond and F' is an optionally substituted 5- or 6-membered heteroaryl. In some embodiments, E' is optionally substituted $C_1$-$C_6$ alkyl and F' is an optionally substituted 5- or 6-membered heteroaryl.

In some embodiments of Formulae (IIa) or (IIb), D' cannot be a bond, E' cannot be a bond, and F' cannot be H. In some embodiments, D' cannot be a bond, E' cannot be $C_1$-$C_6$ alkyl, and F' cannot be H. In some embodiments, D' cannot be alkyl, E' cannot be $C_1$-$C_6$ alkyl, and F' cannot be H. In some embodiments, D' cannot be alkyl, E' cannot be a bond, and F' cannot be H. In some embodiments, D'-E'-F' cannot be

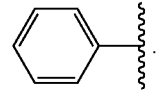

In some embodiments of Formulae (IIa) or (IIb), F' is optionally substituted non-aromatic heterocycle. In some embodiments, F' is optionally substituted piperazine or optionally substituted piperidine.

In some embodiments of Formulae (IIa) or (IIb), D' is —C(O)—, —C(O)O—, —C(O)NR—, —OC(O)—, —OC(O)NR—, —$NRSO_2$—, —NRC(O)—, —$NRSO_2NR$—, —NRC(O)O—, —NRCONR—, or —NRC(NR)NR—; and F' is optionally substituted non-aromatic heterocycle. In some embodiments, D' is —C(O)—, —C(O)O—, —C(O)NR—, —OC(O)—, —OC(O)NR—, —$NRSO_2$—, —NRC(O)—, —$NRSO_2NR$—, —NRC(O)O—, —NRCONR—, or —NRC(NR)NR—; and F' is optionally substituted piperazine or optionally substituted piperidine.

In some embodiments of Formulae (IIa) or (IIb), D' is —C(O)—, —C(O)O—, —C(O)NR—, —OC(O)—, —OC(O)NR—, —NRC(O)—, or —NRC(O)O—; and F' is optionally substituted non-aromatic heterocycle. In some embodiments, D' is —C(O)—, —C(O)O—, —C(O)NR—, —OC(O)—, —OC(O)NR—, —NRC(O)—, or —NRC(O)O—; and F' is optionally substituted piperazine or optionally substituted piperidine.

In some embodiments of a compound of Formulae (Ia), (Ib), (IIa), or (IIb), $R^1$ is an optionally substituted phenyl or an optionally substituted 5- or 6-membered heteroaryl. For example, in some embodiments, $R^1$ is optionally substituted phenyl or optionally substituted pyridine. In some embodiments, $R^1$ is an unsubstituted phenyl or an unsubstituted pyridine. In some embodiments, $R^1$ is a pyridine. In some embodiments the pyridine is attached at the 2 position, the 3 position or the 4 position. In some embodiments the pyridine is attached at the 3 position. In some embodiments, $R^1$ is optionally substituted non-aromatic 3- to 9-membered heterocyclic.

In some embodiments of a compound of Formulae (Ia), (Ib), (IIa), or (IIb), $R^2$ and $R^3$ are independently optionally substituted C$_{1-6}$ alkyl. In some embodiments, R$^2$ and R$^3$ are both methyl. In some embodiments, at least one of R$^2$ and R$^3$ is methyl.

In some embodiments of a compound of Formulae (Ia), (Ib), (IIa), or (Ib), R$^2$ and R$^3$ are independently an optionally substituted C$_1$-C$_9$ cyclic, optionally substituted non-aromatic 3- to 9-membered heterocyclic, or halogen, or R$^2$ and R$^3$ together form an optionally substituted C$_1$-C$_9$ cyclic or optionally substituted non-aromatic 3- to 9-membered heterocyclic ring. In some embodiments, R$^2$ is a C$_1$-C$_6$ alkyl, a C$_3$-C$_9$ cycloalkyl (including cycloalkenyl), or a non-aromatic 3- to 9-membered heterocycle, each of which maybe optionally substituted. In some embodiments, R$^2$ is a C$_1$-C$_6$ alkyl, a C$_3$-C$_9$ cycloalkyl (including cycloalkenyl), or a non-aromatic 3- to 9-membered heterocycle, each of which maybe optionally substituted and R$^3$ is H.

In some embodiments of a compound of Formulae (Ia), (Ib), (IIa), or (IIb), R$^2$ and R$^3$ together form an optionally substituted C$_{3-9}$ cyclic or optionally substituted 3- to 9-membered heterocyclic ring, for example, a C$_3$-C$_{10}$ cycloalkyl (including cycloalkenyl), or a heterocycle, each of which maybe optionally substituted. Exemplary individual embodiments when R$^2$ and R$^3$ together form an optionally substituted C$_{3-9}$ cyclic or optionally substituted 3- to 9-membered heterocyclic ring, include cyclopropyl, cyclobutyl, cyclopentyl, cyclohexyl, cyclopentene, and cyclohexene, each of which may be optionally substituted, for example, by one or more deuterium or fluorine moiety. Other embodiments include bicyclic structures, such as:

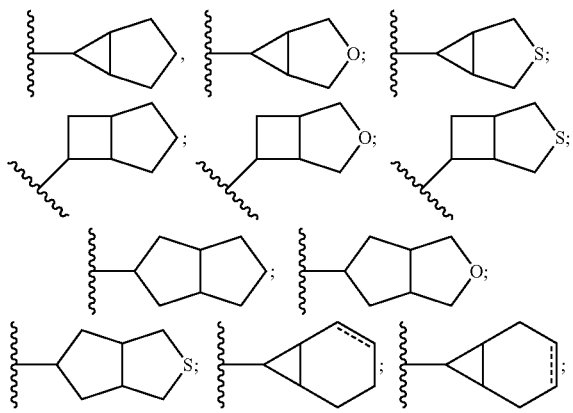

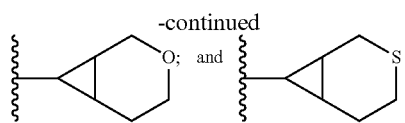

one or more of the dashed bonds may optionally be a double bond and ⸱ indicates attachment to Z. In some embodiments, R$^2$ and R$^3$ together form a cyclopropyl, cyclopentyl or cyclohexene. In some embodiments, R$^2$ and R$^3$ together form a cyclopropyl. In some embodiments, R$^2$ and R$^3$ together form a cyclopentyl. In some embodiments, R$^2$ and R$^3$ together form a cyclohexene.

In some embodiments of a compound of Formulae (Ia), (Ib), (IIa), or (IIb), one or more hydrogens in R$^2$ or R$^3$, or in both R$^2$ and R$^3$ are replaced with deuterium. In some embodiments, R$^2$ and R$^3$ form a perdeuterated cycloalkyl ring. In some embodiments, R$^2$ and R$^3$ form a perdeuterated cyclopentane

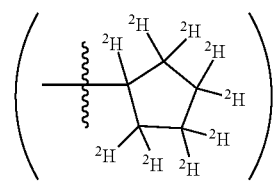

and ⸱ indicates attachment to Z.

In some embodiments of a compound of Formulae (Ia), (Ib), (IIa), or (IIb), one or more hydrogens is replaced with deuterium. In some embodiments,

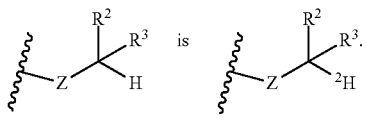

In some embodiments of a compound of Formulae (Ia), (Ib), (IIa), or (Ib), the triazole is attached to the phenyl ring at the para position.

In some embodiments, the compounds of the present disclosure are selected from the compounds of Table I (shown below) or a stereoisomer thereof, or a pharmaceutically acceptable salt or prodrug thereof.

TABLE I

| Entry | Compound | Analytical Data; M + H (LC-HRMS) | P97 Biomol Green™; 200 μM ATP; IC$_{50}$ (μM) |
|---|---|---|---|
| 1 | | 694.2731 | <0.05 |

TABLE I-continued
| Entry | Compound | Analytical Data; M + H (LC-HRMS) | P97 Biomol Green ™; 200 μM ATP; IC$_{50}$ (μM) |
|---|---|---|---|
| 2 | 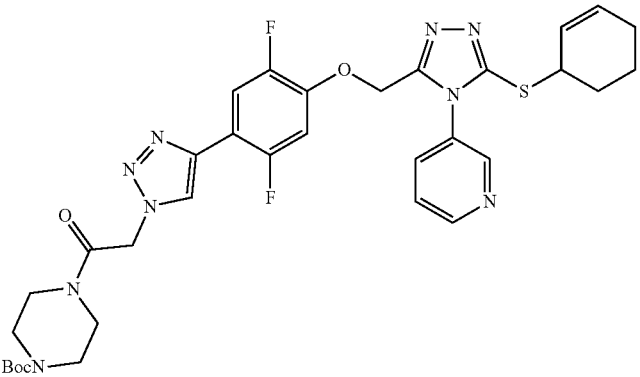 [SMILES: CC(C)(C)OC(=O)N1CCN(C(=O)Cn2cc(-c3cc(F)c(OCc4nnc(SC5C=CCCC5)n4-c4cccnc4)cc3F)nn2)CC1] | 694.2735 | <1 |
| 3 | 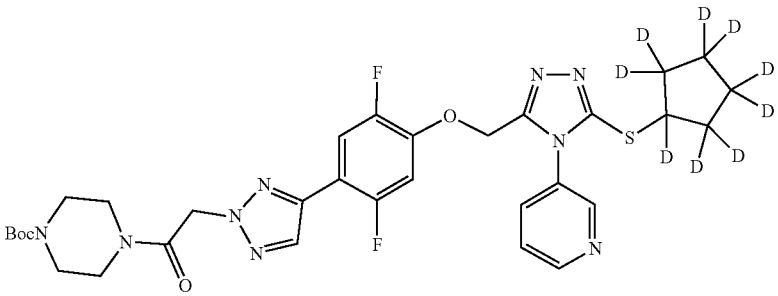 | 691.3292 | <0.05 |
| 4 | 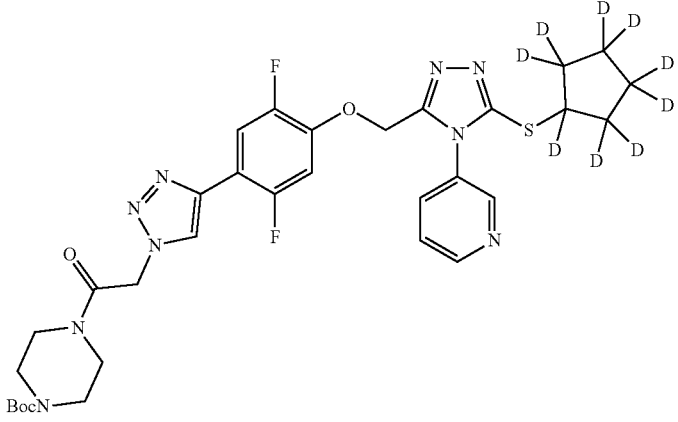 [SMILES: [2H]C1([2H])C([2H])([2H])C([2H])([2H])C([2H])(Sc2nnc(COc3cc(F)c(-c4cn(CC(=O)N5CCN(C(=O)OC(C)(C)C)CC5)nn4)cc3F)n2-c2cccnc2)C1([2H])[2H]] | 691.3297 | <1 |
| 5 | 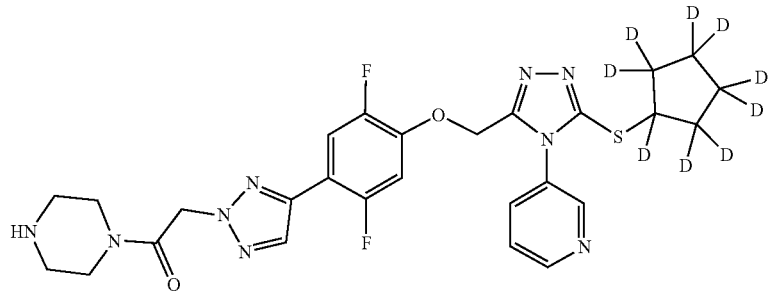 | 591.2766 | <0.05 |

TABLE I-continued

| Entry | Compound | Analytical Data; M + H (LC-HRMS) | P97 Biomol Green ™; 200 μM ATP; IC$_{50}$ (μM) |
|---|---|---|---|
| 6 | | 591.2773 | <1 |
| 7 | | 608.2357 | <0.05 |
| 8 | | 680.2936 | <0.1 |
| 9 | | 512.1676 | <0.05 |
| 10 | | 652.2624 | <0.05 |

TABLE I-continued

| Entry | Compound | Analytical Data; M + H (LC-HRMS) | P97 Biomol Green ™; 200 μM ATP; IC$_{50}$ (μM) |
|---|---|---|---|
| 11 | | 569.1889 | <0.05 |
| 12 | | 638.2471 | <0.1 |
| 13 | | 608.2360 | <0.05 |
| 14 | | 602.2143 | <1 |
| 15 | | 512.1677 | <0.05 |

TABLE I-continued

| Entry | Compound | Analytical Data; M + H (LC-HRMS) | P97 Biomol Green ™; 200 μM ATP; IC$_{50}$ (μM) |
|---|---|---|---|
| 16 | | 694.2726 | <1 |
| 17 | | 694.2733 | <0.05 |
| 18 | | 512.1678 | <1 |
| 19 | | 652.2624 | <1 |
| 20 | | 540.1621 | <0.05 |

TABLE I-continued

| Entry | Compound | Analytical Data; M + H (LC-HRMS) | P97 Biomol Green™; 200 μM ATP; IC$_{50}$ (μM) |
|---|---|---|---|
| 21 | | 526.1467 | <0.1 |
| 22 | | 622.2523 | <0.05 |
| 23 | | 540.1629 | <0.05 |

II. Methods of Treatment

In some embodiments, the compounds of the present disclosure have a Biomol Green™ IC$_{50}$ value of less than about 25 μM, meaning that at a concentration of 25 μM, the compounds inhibit the activity of p97 by at least about half, e.g., about 50%. In other embodiments, the compounds inhibit the activity of p97 in the assay by more than half, such as for example about 55%, about 60%, about 65%, about 70%, about 75%, about 80%, about 85%, or about 90%. Biomol Green (Enzo) is a bioluminescent, homogeneous assay that measures ADP formed from a biochemical reaction. Because of its high sensitivity, the assay is suitable for monitoring enzyme activities at very early substrate conversions requiring very low amount of enzymes.

This is critical since inhibitor potency has to be demonstrated at the cellular level where ATP is present at millimolar concentrations. The assay procedure used may be the same as in Zhang et al., "Altered cofactor regulation with disease-associated p97/VCP mutations," *Proc. Natl. Acad. Sci. USA*, 112(14), E1705-E1714 (2015).

One aspect of the present technology includes methods of modulating p97 in a subject in need thereof. In some embodiments, the treatment of the subject in need thereof comprises administering a compound of the present disclosure (e.g., a compound of Formulae (Ia), (Ib), (IIa), or (IIb), or Table I) to the subject suspected of, or already suffering from elevated activity of p97, in an amount sufficient to cure, or at least partially arrest, the symptoms of elevated activity of p97. As such, some embodiments of the disclosure include methods of treating a subject in need thereof who is suffering from, suspected as having, or at risk of having elevated activity of p97.

In some embodiments, modulation of p97 includes allosteric modulation of p97. In some embodiments, modulation of p97 can be understood as activation of p97 or inhibition of p97. In some embodiments, modulation of p97 leads to at least about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100%, including increments therein, increase or decrease in p97 activity. In some embodiments, modulation of p97 leads to at least about 2-, about 3-, about 4-, about 5-, about 6-, about 7-, about 8-, about 9-, about 10-, about 15-, about 20-, about 25-, about 30-, about 35-, about 40-, about 45-, about 50-, about 55-, about 60-, about 65-, about 70-, about 75-, about 80-, about 85-, about 90-, about 95-, about 100-, about 200-, about 300-, about 400-, about 500-, about 600-, about 700-, about 800-, about 900-, or about 1000-fold, including increments therein, increase or decrease in p97 activity.

Another aspect of the present technology includes methods of inhibiting p97 in a subject in need thereof. In some embodiments, the treatment of the subject in need thereof comprises administering a compound of the present disclosure (e.g., a compound of Formulae (Ia), (Ib), (IIa), or (IIb), or Table I) to the subject suspected of, or already suffering from elevated activity of p97, in an amount sufficient to cure, or at least partially arrest, the symptoms of elevated activity of p97. As such, some embodiments of the disclosure include methods of treating a subject in need thereof who is suffering from, suspected as having, or at risk of having elevated activity of p97.

Another aspect of the present technology includes methods of treating cancers or neurodegenerative disorders susceptible to treatment by p97 inhibition in a subject diagnosed as having, suspected as having, or at risk of having cancer or a neurodegenerative disorder susceptible to treatment by p97 inhibition. As such, some embodiments of the disclosure include methods of treating a subject in need thereof who is suffering from, suspected as having, or at risk of having cancer or a neurodegenerative disorder susceptible to treatment by p97 inhibition. In some embodiments, the treatment of the subject in need thereof comprises administering a compound of the present disclosure (e.g., a compound of Formulae (Ia), (Ib), (IIa), or (Ib), or Table I) to the subject suspected of, or already suffering from cancer or a neurodegenerative disorder susceptible to treatment by p97 inhibition, in an amount sufficient to cure, or at least partially arrest, the symptoms of the disease, including its complications and intermediate pathological phenotypes in development of the disease.

Another aspect of the present technology includes methods of treating cancers or neurodegenerative disorders susceptible to treatment by p97 modulation in a subject diagnosed as having, suspected as having, or at risk of having cancer or a neurodegenerative disorder susceptible to treatment by p97 modulation. As such, some embodiments of the disclosure include methods of treating a subject in need thereof who is suffering from, suspected as having, or at risk of having cancer or a neurodegenerative disorder susceptible to treatment by p97 modulation. In some embodiments, the treatment of the subject in need thereof comprises administering a compound of the present disclosure (e.g., a compound of Formulae (Ia), (Ib), (IIa), or (IIb), or Table I) to the subject suspected of, or already suffering from cancer or a neurodegenerative disorder susceptible to treatment by p97 modulation, in an amount sufficient to cure, or at least partially arrest, the symptoms of the disease, including its complications and intermediate pathological phenotypes in development of the disease.

In some embodiments, cancers susceptible to treatment by p97 inhibition or p97 modulation include but are not limited to solid tumor cancers, non-small cell lung carcinoma, multiple myeloma, or mantle cell lymphoma. In some embodiments, cancers susceptible to treatment by p97 inhibition or p97 modulation include a solid tumor. See Valle et al., "Critical Role of VCP/p97 in the Pathogenesis and Progression of Non-Small Cell Lung Carcinoma," *PlosOne*, 6(12): e29073 (2011) and Deshaies, "Proteotoxic crisis, the ubiquitin-proteasome system, and cancer therapy," BMC Biology 12(94), 1 (2014).

In some embodiments, neurodegenerative disorders susceptible to treatment by p97 inhibition or p97 modulation include but are not limited to inclusion body myopathy (IBM), Paget's disease of the bone (PDB), frontotemporal dementia (FTD) and amyotrophic lateral sclerosis (ALS)). Neurodegenerative disorders also include subjects having p97 mutations, and symptoms manifesting as, for example, Parkinsonism, ataxia, cataracts, dilated cardiomyopathy, hepatic fibrosis, and hearing loss.

Another aspect of the present technology includes methods of treating antibacterial and/or antiviral infection susceptible to treatment by p97 modulation in a subject diagnosed as having, suspected as having, or at risk of having antibacterial and/or antiviral infection susceptible to treatment by p97 modulation. As such, some embodiments of the disclosure include methods of treating a subject in need thereof who is suffering from, suspected as having, or at risk of having antibacterial and/or antiviral infection susceptible to treatment by p97 modulation. In some embodiments, the treatment of the subject in need thereof comprises administering a compound of the present disclosure (e.g., a compound of Formulae (Ia), (Ib), (IIa), or (IIb), or Table I) to the subject suspected of, or already suffering from antibacterial and/or antiviral infection susceptible to treatment by p97 modulation, in an amount sufficient to cure, or at least partially arrest, the symptoms of the disease, including its complications and intermediate pathological phenotypes in development of the disease.

The compound may be included in a pharmaceutical formulation, such as those disclosed herein, and may be administered in any pharmaceutically acceptable manner, including methods of administration described herein.

The compounds useful in the methods of the present technology are administered to a mammal in an amount effective in treating or preventing elevated activity of p97, cancers susceptible to treatment by p97 inhibition or p97 modulation, or neurodegenerative disorders susceptible to treatment by p97 inhibition or p97 modulation. The therapeutically effective amount can be determined by methods known in the art.

An effective amount of a compound useful in the methods of the present technology, for example in a pharmaceutical composition, may be administered to a mammal in need thereof by any of a number of well-known methods for administering pharmaceutical compounds. The compound may be administered systemically or locally. In one embodiment, the compound is administered intravenously. For example, the compounds useful in the methods of the present technology may be administered via rapid intravenous bolus injection. In some embodiments, the compound is administered as a constant rate intravenous infusion. The compound may also be administered orally, topically, intranasally, intramuscularly, subcutaneously, or transdermally. Other routes of administration include intracerebroventricularly or intrathecally. Intracerebroventiculatly refers to administration into the ventricular system of the brain. Intrathecally refers to administration into the space under the arachnoid membrane of the spinal cord.

The compounds useful in the methods of the present technology may also be administered to mammals by sustained or controlled release, as is known in the art. Sustained release administration is a method of drug delivery to achieve a certain level of the drug over a particular period of time. The level typically is measured by serum or plasma concentration.

In one preferred embodiment, the compounds are administered orally. In one preferred embodiment, the compounds are administered intravenously. In one preferred embodiment, the compounds are administered at less than about 1 gram per day. In other embodiments of the present technology, the compounds are administered at less than about 10, at less than about 9, at less than about 8, at less than about 7, at less than about 6, at less than about 5, less than about 4, less than about 3, less than about 2, less than about 1, less than about 0.9, less than about 0.8, less than about 0.7, less than about 0.6, less than about 0.5, less than about 0.4, less than about 0.3, less than about 0.2, or less than about 0.1 grams per day, or any amount in between these values.

III. Pharmaceutical Formulations

For oral administration, liquid or solid dose formulations may be used. Some non-limiting examples of oral dosage formulations include tablets, gelatin capsules, pills, troches, elixirs, suspensions, syrups, wafers, chewing gum and the like. The compounds can be mixed with a suitable pharmaceutical carrier (vehicle) or excipient as understood by practitioners in the art. Non-limiting examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the compounds useful in the methods of the present technology may utilize conventional diluents, carriers, or excipients etc., such as are known in the art can be employed to deliver the compounds. For example, the formulations may comprise one or more of the following: a stabilizer, a surfactant (such as a nonionic, ionic, anionic, cationic, or zwitterionic surfactant), and optionally a salt and/or a buffering agent. The compound may be delivered in the form of a solution or in a reconstituted lyophilized form.

In some embodiments, the stabilizer may, for example, be an amino acid, such as for instance, glycine or an oligosaccharide, such as for example, sucrose, tetralose, lactose or a dextran. Alternatively, the stabilizer may be a sugar alcohol, such as for instance, mannitol, sorbitol, xylitol, or a combination thereof. In some embodiments, the stabilizer or combination of stabilizers constitutes from about 0.1% to about 10% by weight of the formulation, or any percentage in between these two values.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) to about 10% (w/v), or any percentage in between these two values.

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5, or any pH in between these two values. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the compounds useful in the methods of the present technology may additionally comprise one or more conventional additives. Some non-limiting examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits. In some embodiments, the mammal is a human.

IV. Combination Therapy

In some embodiments, the compounds of the present disclosure may be combined with one or more additional therapies for the prevention or treatment of a disease or condition amenable to treatment by inhibition of p97 or modulation of p97, including but not limited to inclusion body myopathy (IBM), Paget's disease of the bone (PDB), frontotemporal dementia (FTD), and amyotrophic lateral sclerosis (ALS). Additional therapeutic agents or active agents include, but are not limited to, alkylating agents, nitrosoureas, antimetabolites, antitumor antibiotics, plant vinca alkaloids, and steroid hormones.

The multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

For example, drugs useful in treating inclusion body myopathy (IBM) include, but are not limited to, Arimoclomol, medications that suppress the immune system, such as corticosteroids (e.g., prednisone), immunosuppressants (e.g., methotrexate, azathioprine, cyclophosphamide, and cyclosporine), oxandrolone, Acthar (preparation of ACTH in 16% gelatin formulation), intravenous immune globulin (IVIG), biological agents (e.g., an antibody against myostatin, MYO-029), anti-TNF agents, Rituximab (rituxan), and Alemtuzumab (campath).

Drugs useful in treating Paget's disease of the bone (PDB) include, but are not limited to, Calcitonin (salmon and human), Bisphosphonates (e.g., etidronate, clodronate, aminobisphosphonates, alendronate, risedronate, pamidronate, zoledronate, tiludronate), zoledronic acid, densosumab, calcium, vitamin D, and painkillers (e.g., ibuprofen and paracetamol).

Drugs useful in treating frontotemporal dementia (FTD) include, but are not limited to, Cholinesterase inhibitors, such as donepezil (Aricept®), rivastigmine (Exelon®) and galantamine (Razadyne®), antidepressants (e.g., fluoxetine (Prozac®), sertraline (Zoloft®), paroxetine (Paxil®), fluvoxamine (Luvox®), citalopram (Celexa®), escitalopram (Lexapro®), trazodone (Desyrel®), venlafaxine (Effexor®), duloxetine (Cymbalta®), bupropion (Wellbutrin®), mirtazepine (Remeron®)), antipsychotics (e.g., olanzepine (Zyprexa®), quetiapine (Seroquel® or Ketipinor®), risperidone (Risperdal®), ziprasidone (Geodon®), aripiprazole (Abilify®), paliperidone (INVEGA®)), valproic acid and divalproex sodium (Depacon™, Depakene®, Depakote®, Depakote® ER), carbamazepine (Tegretol®), gabapentin (Neurontin®), and Memantine (Namenda®).

Drugs useful in treating amyotrophic lateral sclerosis (ALS) include, but are not limited to, riluzole (Rilutek), Radicava (edaravone), pain relievers or muscle relaxants such as baclofen (Gablofen, Kemstro, Lioresal) or diazepam (Diastat, Valium).

In some embodiments, the compounds of the present disclosure can be combined with proteosome inhibitors. In another embodiment, the compounds of the present disclosure can be combined with other anti-cancer agents. In some embodiments, the compounds of the present disclosure can be combined with heat shock protein (HSP) inhibitors. In some embodiments, the compounds of the present disclosure can be combined with two or more of proteasome inhibitors, HSP inhibitors, and other anti-cancer agents.

V. Definitions

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes.

In determining whether a number is near to or approximately a specifically recited number, the near or approximating unrecited number may be a number which, in the context in which it is presented, provides the substantial equivalent of the specifically recited number.

Generally, reference to a certain element such as hydrogen or H is meant to include all isotopes of that element. For example, if a group is defined to include hydrogen or H, it also includes deuterium and tritium. Hence, isotopically labeled compounds are within the scope of the present technology. In some embodiments, one or more of the H in a compound of Formulae (Ia), (Ib), (IIa), or (IIb), or Table I is replaced with a deuterium.

In general, "substituted" refers to an organic group (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. The present disclosure is understood to include embodiments where, for instance a "substituted alkyl" optionally contains one or more alkene and/or alkyne. A substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; aryl groups; heteroaryl groups; cycloalkyl groups; heterocyclyl groups; carbonyls (oxo); carboxyls; esters; carbamates; urethanes; ureas; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocycle and heteroaryl groups also include rings and fused ring systems in which a bond to a hydrogen atom is replaced with a bond to a carbon atom. Therefore, substituted cycloalkyl, aryl, heterocycle and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. As stated above, the present disclosure is understood to include embodiments where, for instance a "substituted alkyl" optionally contains one or more alkene and/or alkyne.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-di-substituted cyclohexyl groups, which may be substituted with substituents such as those listed above. In some embodiments, a cycloalkyl group has one or more alkene bonds, but is not aromatic.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heterocycle groups include aromatic (also referred to as heteroaryl) and non-aromatic ring compounds containing 3 or more ring members, of which one or more is a heteroatom such as, but not limited to, N, O, S or B. In some embodiments, heterocycle groups include 3 to 20 ring members, whereas other such groups have 3 to 6, 3 to 10, 3 to 12, or 3 to 15 ring members.

Heterocycle groups encompass unsaturated, partially saturated and saturated ring systems, such as, for example, imidazolyl, imidazolinyl and imidazolidinyl groups. The phrase "heterocycle group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocycle groups that have other groups, such as alkyl, oxo or halo groups, bonded to one of the ring members. Rather, these are referred to as "substituted heterocycle groups". Heterocycle groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocycle groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, S or B. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like.

Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The term "amine" (or "amino") as used herein refers to —NHR* and —NR*R* groups, wherein R* are independently hydrogen, or a substituted or unsubstituted alkyl, alkenyl, alkynyl, cycloalkyl, aryl, aralkyl, heterocyclylalkyl or heterocycle group as defined herein. In some embodiments, the amine is $NH_2$, methylamino, dimethylamino, ethylamino, diethylamino, propylamino, isopropylamino, phenylamino, or benzylamino. In some embodiments, the two R* groups together with the nitrogen to which they are attached form an optionally substituted heterocyclic ring. In further embodiments, the optionally substituted heterocyclic ring is an optionally substituted piperazine, optionally substituted piperidine, or optionally substituted pyrrolidine.

The term "amide" refers to a —NR*R*C(O)— group wherein R* each independently refer to a hydrogen, ($C_1$-$C_5$)alkyl, or ($C_3$-$C_6$)aryl, or the two R* together with the nitrogen to which they are attached form an optionally substituted heterocyclic ring.

Those of skill in the art will appreciate that compounds of the present technology may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the present technology encompasses any tautomeric, conformational isomeric, optical isomeric and/or geometric isomeric forms of the compounds having one or more of the utilities described herein, as well as mixtures of these various different forms.

As readily understood by one skilled in the art, a wide variety of functional groups and other structures may exhibit tautomerism, and all tautomers of compounds as described herein are within the scope of the present technology.

Stereoisomers of compounds, also known as "optical isomers," include all chiral, diastereomeric, and racemic forms of a structure, unless the specific stereochemistry is expressly indicated. Thus, compounds used in the present technology include enriched or resolved optical isomers at any or all stereogenic atoms as are apparent from the depictions. Both racemic and diastereomeric mixtures, as well as the individual optical isomers can be isolated or synthesized so as to be substantially free of their enantiomeric or diastereomeric partners, and these are all within the scope of the present technology.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present technology which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present technology can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present technology contemplates sodium, potassium, magnesium, and calcium salts of the compounds of the compounds of the present technology and the like.

The term "solvates" is used in its broadest sense. For example, the term solvates includes hydrates formed when a compound of the present technology contains one or more bound water molecules.

Certain compounds within the scope of the disclosure are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," Methods in Enzymology 112: 309-23 (1985); Bodor, N., "Novel Approaches in Prodrug Design," *Drugs of the Future*, 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), Goodman and Gilmans, THE PHARMACOLOGICAL BASIS OF THERAPEUTICS, 8th ed., McGraw-Hill (1992). In some embodiments, the "prodrug" is a compound that generally converts to an active compound of the present disclosure within a physiological environment (e.g., stomach, colon, blood). Prodrugs include esters, carbonates, carbamates, oximes of active alcohols (and/or acids for esters), amides, carbamates, ureas, oximes, Mannich bases, imines of amines (and/or acids for amides), carbondithianes of active thiols, conjugates of reactive species such as a,b-unsaturated carbonyl derivatives. The selection and synthesis of prodrugs include strategies such as those in: Karaman, R., "Prodrugs design based on inter- and intra-molecular chemical processes," *Chem. Biol. DrugDes.*, 82: 643-668 (2013); Huttunen et al., "Prodrugs-from serendipity to rational design," *Pharmacol. Rev.*, 63, 750-771 (2011); Blencowe et al., "Self-immolative linkers in polymeric delivery systems," *Polym. Chem.*, 2: 773-790 (2011); Arpicco et al., "Anticancer prodrugs: An overview of major strategies and recent developments," *Curr. Top. Med. Chem.* (Sharjah, UnitedArab Emirates), 11: 2346-2381 (2011); Tietze et al., "Antibody-directed enzyme prodrug therapy: A promising approach for a selective treatment of cancer based on prodrugs and monoclonal antibodies" *Chem. Biol. Drug Des.*, 74: 205-211 (2009); Simplicio et al., "*Prodrugs for amines,*" *Molecules*, 13: 519-547 (2008); Rautio et al., "Prodrugs: Design and clinical applications," *Nat. Rev. Drug Discovery*, 7: 255-270 (2008); Lee et al., "Pro-drug and Antedrug: Two Diametrical Approaches in Designing Safer Drugs," *Arch. Pharm. Res.*, 25: 111-136 (2002); and Lee, *Chem. Biol. Drug Des.*, 82: 643-668 (2013).

Generally, reference to a certain moiety capable of being protected (such as hydroxy, amine, carbonyl, etc.) includes the protected groups in some embodiments of the disclosure. For example, in some embodiments, an —OH moiety as included herein also includes —OP, where P is a protecting group. Protecting groups, as referred to herein may be selected by one of ordinary skill in the art, and include the groups and strategies set forth in the art, for example, those such as described in R. Larock, Comprehensive Organic Transformations, VCH Publishers (1989); T. W. Greene and P. G. M. Wuts, Greene's protective groups in organic synthesis, John Wiley & Sons (2006); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Unless defined otherwise, all technical and scientific terms used herein have the same meaning as commonly understood by one of ordinary skill in the art to which this present technology belongs. Although any methods and materials similar or equivalent to those described herein can also be used in the practice or testing of the present technology, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the present technology. The upper and lower limits of these smaller ranges may independently be included in the smaller ranges and are also encompassed within the present technology, subject to any specifically excluded limit in the stated range. Where the stated range includes one or both of the limits, ranges excluding either or both of those included limits are also included in the present technology.

This disclosure is not limited to particular embodiments described, as such may, of course, vary. It is also to be understood that the terminology used herein is for the purpose of describing particular embodiments only, and is not intended to be limiting, since the scope of the present technology will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present technology. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present technology is not entitled to antedate such publication by virtue of prior invention. Further, the dates of publication provided may be different from the actual publication dates which may need to be independently confirmed.

VI. Working Examples

The present technology is further illustrated by the following examples, which should not be construed as limiting in any way.

General information. All non-aqueous reactions were carried out under a nitrogen atmosphere in oven- or flame-dried glassware unless otherwise noted. Anhydrous tetrahydrofuran and diethyl ether were distilled from sodium benzophenone ketyl; anhydrous dichloromethane and toluene were distilled from $CaH_2$; alternatively, the same solvents were obtained from a solvent purification system using alumina columns. All other solvents and reagents were used as obtained from commercial sources without further purification unless noted. Reactions were monitored via TLC using 250 μm pre-coated silica gel 60 $F_{254}$ plates, which were visualized with 254 nm and/or 365 nm UV light and by staining with $KMnO_4$ (1.5 g $KMnO_4$, 10 g $K_2CO_3$, and 1.25 mL 10% NaOH in 200 mL water), cerium molybdate (0.5 g $Ce(NH_4)_2(NO_3)_6$, 12 g $(NH_4)_6M_{o7}O_{24} \cdot 4H_2O$, and 28 mL conc. $H_2S_4$ in 235 mL water), or vanillin (6 g vanillin and 1.5 mL conc. $H_2SO_4$ in 100 mL EtOH). Flash chromatography was performed with SiliCycle silica gel 60 (230-400 mesh) or with ISCO MPLC. HRMS data were obtained on a Thermo Scientific Exactive HRMS coupled to a Thermo Scientific Accela HPLC system using a 2.1×50 mm 3.5 μm Waters XTerra Cis column eluting with $MeCN/H_2O$ containing 0.1% formic acid.

General Synthetic Methods

The compounds of the present disclosure can be prepared using the following general methods and procedures. The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley, and Sons, 1991), *Rodd's Chemistry of Carbon Compounds*, Volumes 1-5, and Supplementals (Elsevier Science Publishers, 1989), Organic Reactions, Volumes 1-40 (John Wiley, and Sons, 1991), *March's Advanced Organic Chemistry*, (John Wiley, and Sons, 5$^{th}$ Edition, 2001), and *Larock's Comprehensive Organic Transformations* (VCH Publishers Inc., 1989).

More specifically, compounds provided herein can be synthesized as shown in the following Examples, and following adaptations of the methods described therein and/or methods known to a skilled artisan and/or by using different commercially available starting materials.

Example 1. Synthesis of 1,2,3-Triazoles 15ac, 15bc, 15bd, 16bc, 16bd, 17, 19e, 19f, 20 and 21 (Scheme 1)

Scheme 1.

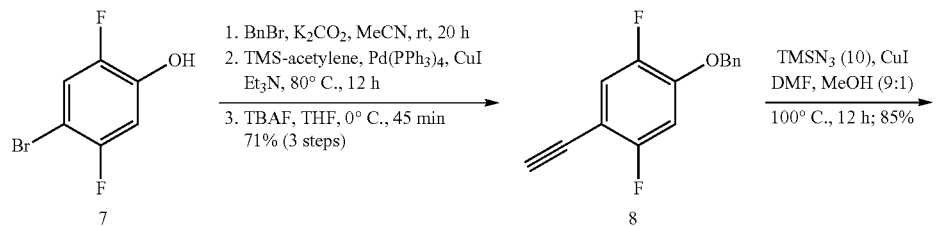

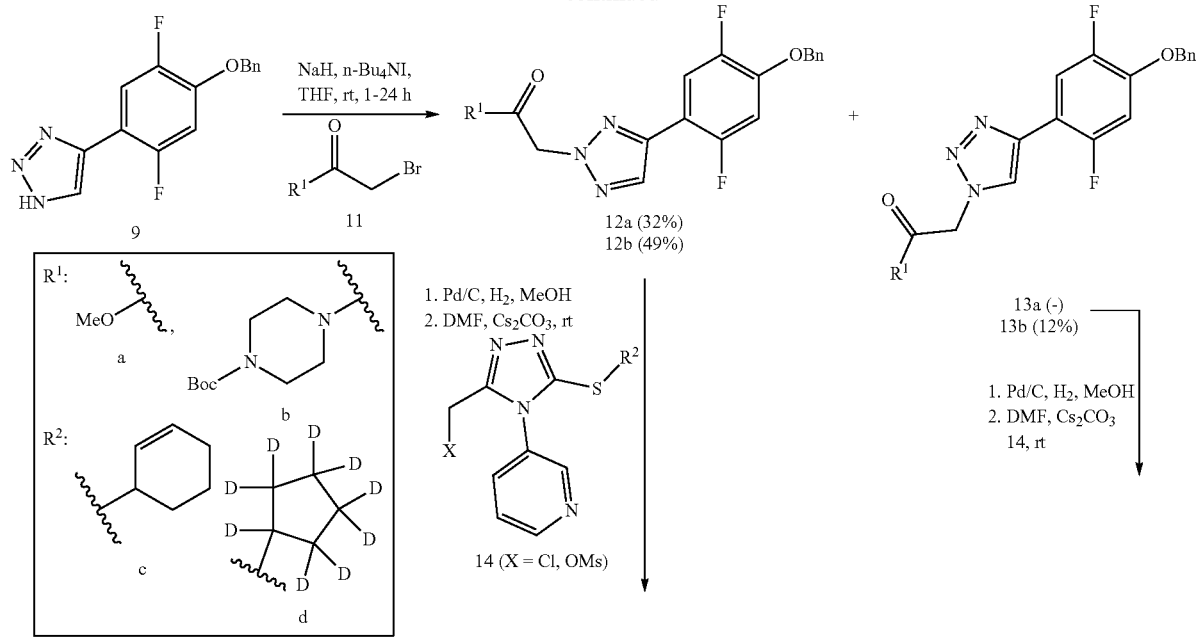
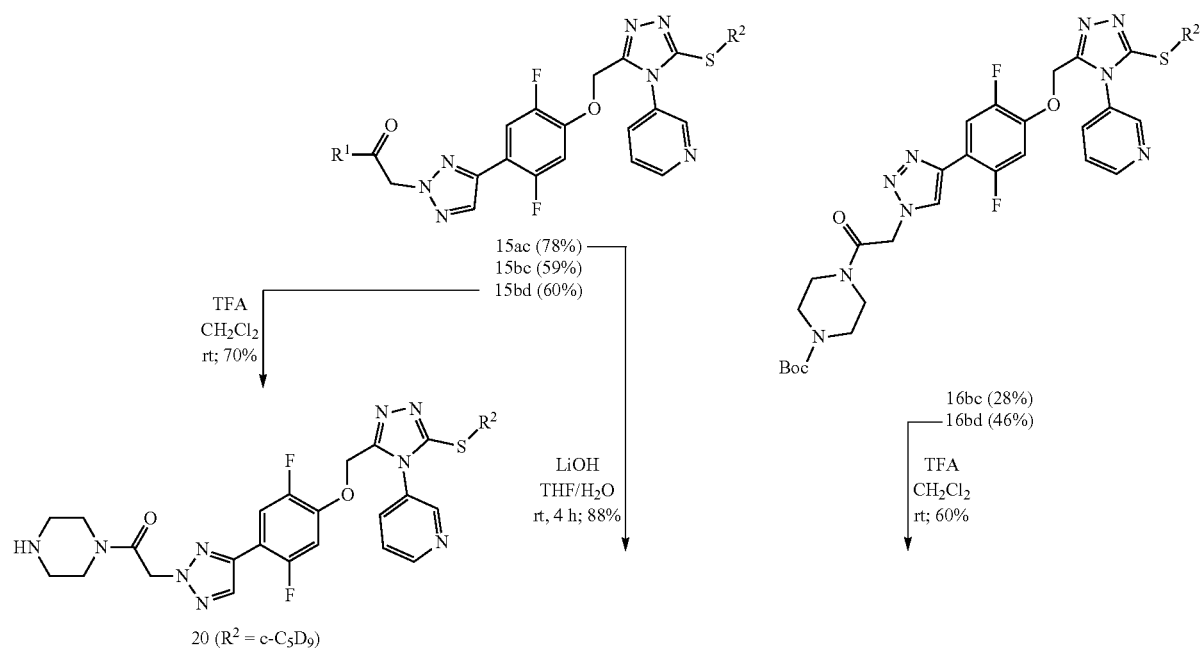

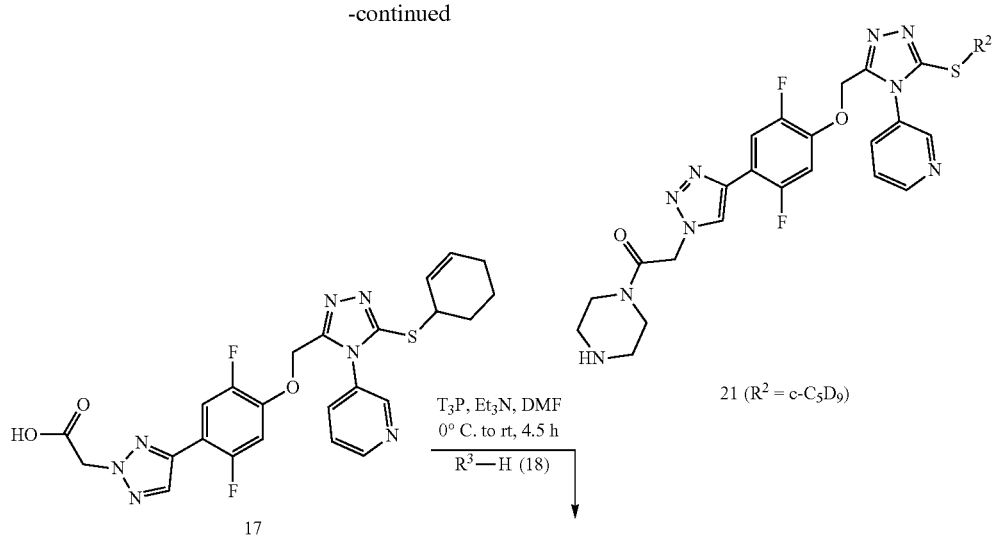

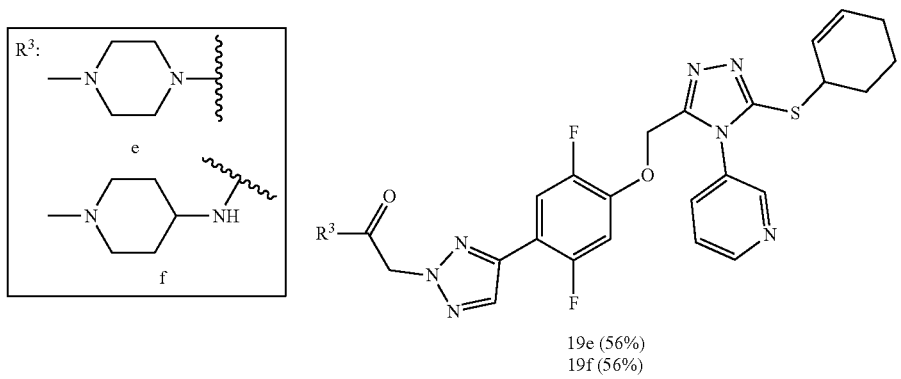

Following Scheme 1, commercially available 4-bromo-2,5-difluorophenol 7 was benzylated and coupled with trimethylsilylacetylene under Sonogashira conditions. Cleavage of the TMS group provided the terminal alkyne 8 in 71% yield. The 1,2,3-triazole building block 9 was obtained in 85% yield by the 1,3-dipolar cycloaddition with azide 10 in a 9:1 mixture of DMF and methanol. N-Alkyation of 1,2,3-triazoles generally provides major substitution at N(2) with some minor product formed by alkylation at N(1). Indeed, treatment of 9 with bromides 11a and 11b gave mainly the N(2)-alkylated ester 12a and amide 12b, respectively. Both of these compounds were debenzylated with Pd/C under an atmosphere of hydrogen gas, and then O-alkylated as the cesium salts with 1,2,4-triazole 14. In addition to the cyclohexenyl thioether 14c, the cyclopentyl thioether 14d (with a perdeutero-cyclopentane) was also used. Methyl ester 15ac was saponified to acid 17, which was further converted to amides 19e and 19f in a T3P-mediated coupling with 1-methylpiperazine (18e) and 1-methylpiperidin-4-amine (18f), respectively. Removal of the Boc protective group from 15bd led to piperazide 20. In the N(1)-alkylated 1,2,3-triazole series, debenzylation of 13b followed by O-alkylation with 14 gave ethers 16bc and 16bd in moderate yields. The Boc group on perdeuterocyclopentyl thioether 16bd was removed to give piperazide 21.

Example 2. Synthesis of 1,2,3-Triazoles 22, 25, and 26 (Scheme 2)
Scheme 2.
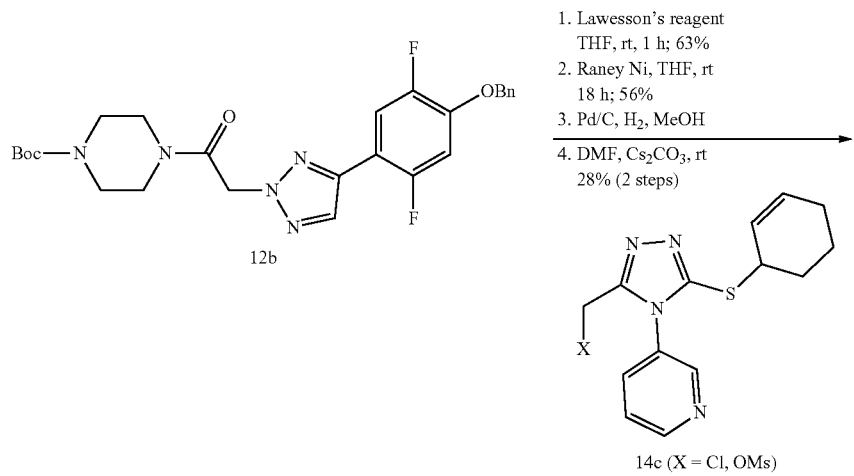
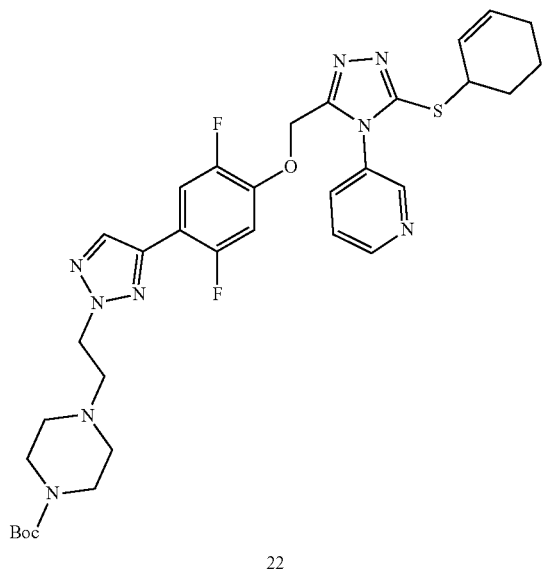
22
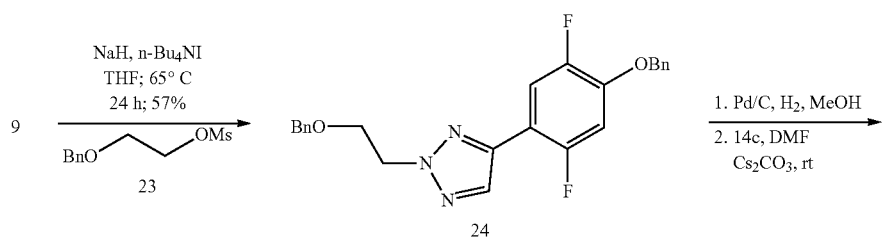

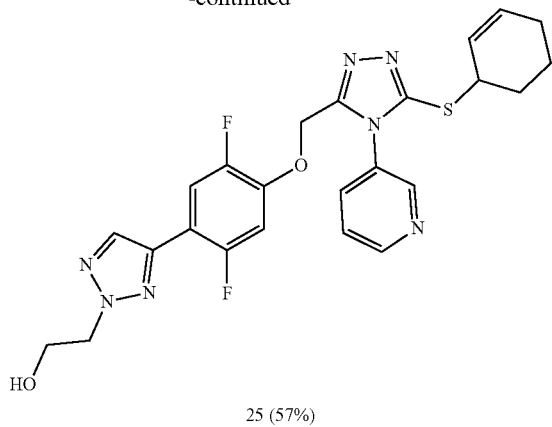

25 (57%)

1. CDI, Et₃N rt, 3 h
2. 18f, 12 h, rt

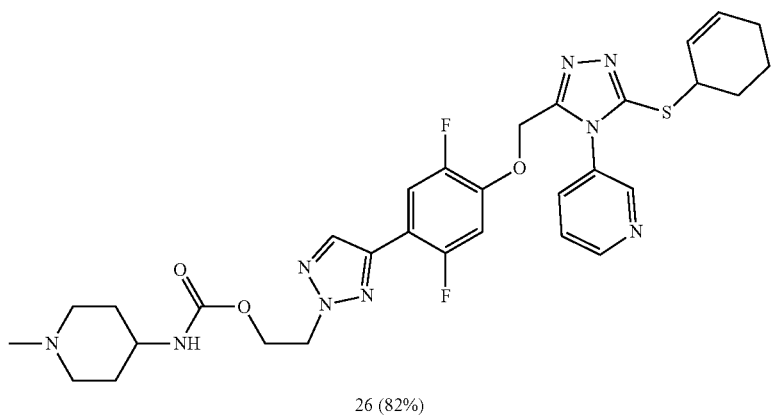

26 (82%)

Following Scheme 2, amide 12b was treated with Lawesson reagent to give the intermediate thioamide, which was reduced with Raney-Nickel, debenzylated under catalytic hydrogenolysis conditions, and alkylated with building block 14c to generate the diamine 22. Alkylation of 9 with mesylate 23 delivered the N(2)-substituted triazole 24 as the sole product, which was debenzylated and selectively alkylated at the phenol with 1,2,4-triazole 14c. The primary alcohol in product 25 was then treated with 1,1'-carbonyldiimidazole (CDI), followed by trapping of the intermediate carbamate with 1-methylpiperidin-4-amine (18f) to yield 26 in 27% from 9.

Example 3. Synthesis of 1,2,3-Triazoles 29 and 30

Scheme 3.

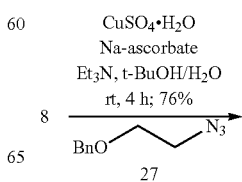

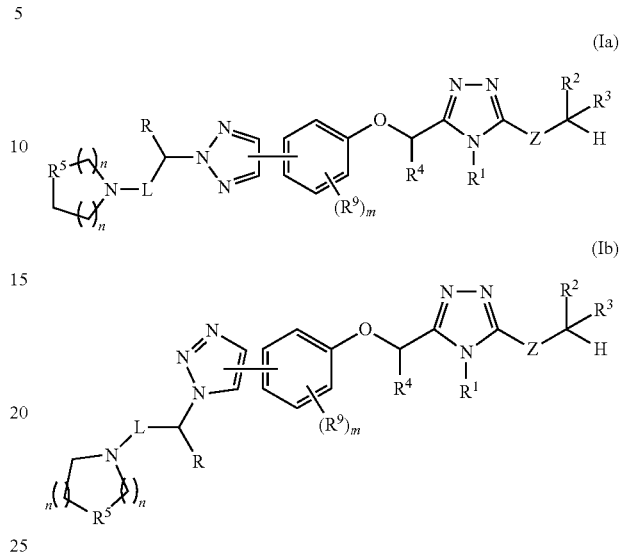

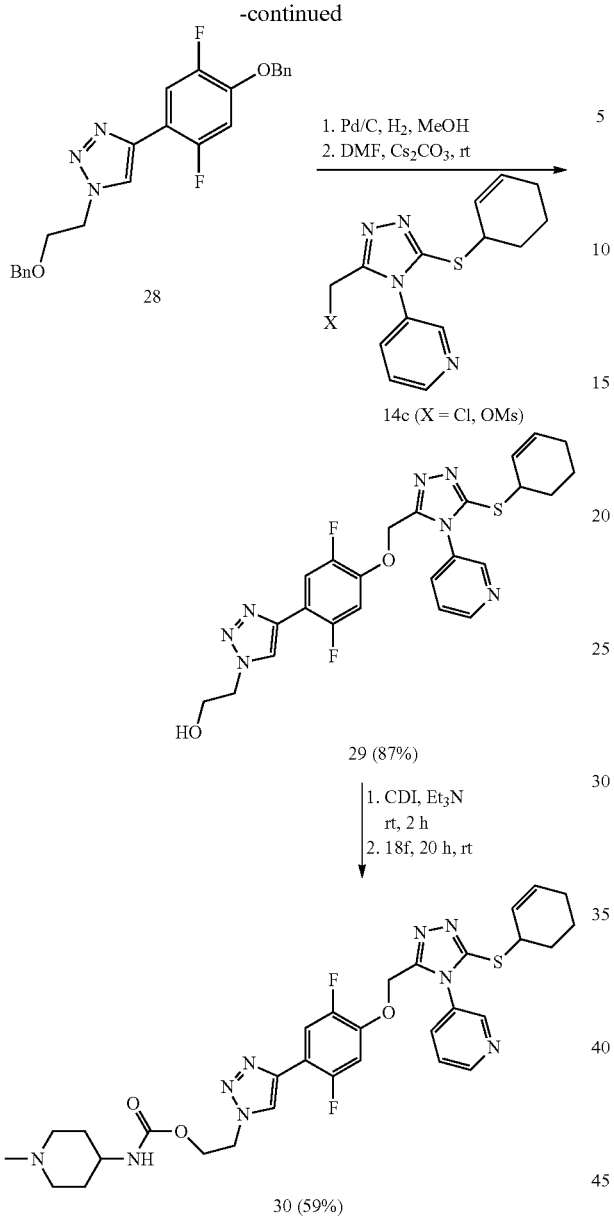

Alkyne 8 was subjected to a 1,3-dipolar cycloaddition with azide 27 to provide intermediate 28 (Scheme 3). O-Debenzylation with catalytic hydrogenolysis and alkylation with the cesium salt of 14c led to ether 29 in 87% yield. This compound was converted to piperidine 30 via the activated carbamate.

Example 4. Assay Methods

The BioMol Green ATPase assay procedure used was that which was disclosed in Zhang, et al., "Altered cofactor regulation with disease-associated p97/VCP mutations," Proc. Natl. Acad. Sci. USA, 112(14), E1705-E1714 (2015). Table I provides selected results. Compounds also show activity in a cell-based assay such as the ubiquitin assay.

While certain embodiments have been illustrated and described, it should be understood that changes and modifications can be made therein in accordance with ordinary skill in the art without departing from the technology in its broader aspects as defined in the following claims.

The invention claimed is:
1. A compound having the structure of Formula (Ia) or Formula (Ib):

or a stereoisomer thereof, or a pharmaceutically acceptable salt thereof, wherein:

Z is O, $SO_{0-2}$, NR, or $C(R^7)_2$;

L is C(O) or $SO_{1-2}$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

m is 0, 1, 2, 3, or 4;

each n is independently 0, 1, 2, 3, or 4;

$R^5$ is $C(R^6)_2$, $NR^8$, $SO_{0-2}$, or O;

R is independently selected from the group consisting of H, optionally substituted alkyl, and optionally substituted cycloalkyl;

$R^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —N(R$^8$)$_2$; —C(O)-(optionally substituted alkyl); —C(O)O-(optionally substituted alkyl); —C(O)(NR)-(optionally substituted alkyl); —SO$_{0-2}$-(optionally substituted alkyl); —C(O)-(optionally substituted cycloalkyl); —C(O)O-(optionally substituted cycloalkyl); —C(O)(NR)-(optionally substituted cycloalkyl); —SO$_{0-2}$-(optionally substituted cycloalkyl); —C(O)-(optionally substituted aryl); —C(O)O-(optionally substituted aryl); —C(O)(NR)-(optionally substituted aryl); —SO$_{0-2}$-(optionally substituted aryl); —C(O)-(optionally substituted heterocyclic); —C(O)O-(optionally substituted heterocyclic);

—C(O)(NR)-(optionally substituted heterocyclic); and
—SO$_{0-2}$-(optionally substituted heterocyclic);

R$^7$ is independently selected from the group consisting of H, halogen, optionally substituted alkyl, optionally substituted cycloalkyl, —OR, and —N(R)$_2$;

R$^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —SO$_{0-2}$-(optionally substituted alkyl); —C(O)-(optionally substituted cycloalkyl); —C(O)O-(optionally substituted cycloalkyl); —C(O)(NR)-(optionally substituted cycloalkyl); —SO$_{0-2}$-(optionally substituted cycloalkyl); —C(O)-(optionally substituted aryl); —C(O)O-(optionally substituted aryl); —C(O)(NR)-(optionally substituted aryl); —SO$_{0-2}$-(optionally substituted aryl); —C(O)-(optionally substituted heterocyclic); —C(O)O—(optionally substituted heterocyclic); —C(O)(NR)-(optionally substituted heterocyclic); and —SO$_{0-2}$-(optionally substituted heterocyclic); or two R$^8$, together with the nitrogen atom to which they are attached, form an optionally substituted heterocyclic ring; and R$^9$ is independently selected from the group consisting of halogen, nitrile, optionally substituted alkyl, optionally substituted cycloalkyl, —NR$_2$, —SF$_5$, —OR, —CO$_2$R, —SR, —SOR, and —SO$_2$R.

2. The compound of claim 1, wherein R$^9$ is halogen, nitrile, a C$_1$-C$_6$ alkyl, or O-C$_1$-C$_6$ alkyl.

3. The compound of claim 1, wherein:
(a) R$^5$ is NR$^8$; or
(b) R$^5$ is C(R$^6$)$_2$.

4. The compound of claim 1, wherein:
(a) n is 1; and/or
(b) Z is S; and/or
(c) R$^1$ is pyridine; and/or
(d) R$^4$ is H.

5. The compound of claim 1, wherein R$^2$ and R$^3$ together are a cyclopropyl, cyclopentyl, cyclohexene, or a perdeuterated cycloalkyl ring.

6. A compound having the structure of Formula (IIa) or Formula (IIb):

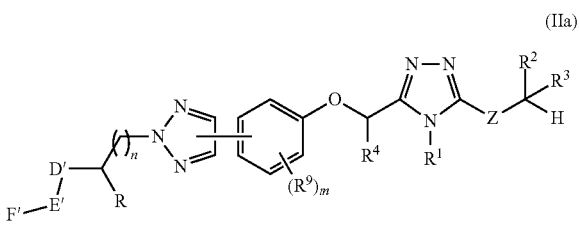

(IIa)

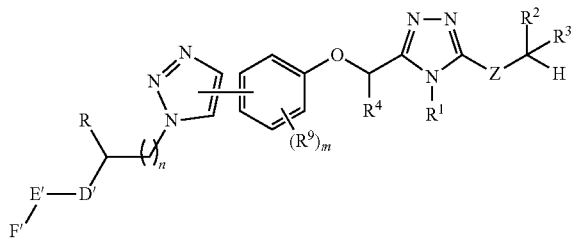

(IIb)

or a stereoisomer thereof, or a pharmaceutically acceptable salt thereof, wherein:

Z is O, SO$_{0-2}$, NR, or C(R$^7$)$_2$;

R$^2$ and R$^3$ are independently an optionally substituted C$_{1-9}$ cyclic, C$_{3-9}$ heterocyclic, or halogen, or R$^2$ and R$^3$ together form an optionally substituted C$_{3-9}$ cyclic or 3- to 9-membered heterocyclic ring;

R$^1$ is optionally substituted phenyl, optionally substituted 5- or 6-membered heteroaryl, or optionally substituted non-aromatic heterocyclic;

R$^4$ is H, C(R$^7$)$_3$, aryl, or heteroaryl;

R is independently selected from the group consisting of H, optionally substituted alkyl, and optionally substituted cycloalkyl;

R$^7$ is independently selected from the group consisting of H, halogen, optionally substituted alkyl, optionally substituted cycloalkyl, —OR, and —N(R)$_2$;

m is 0, 1, 2, 3, or 4;

n is 1, 2, 3, or 4;

R$^9$ is independently selected from the group consisting of halogen, nitrile, optionally substituted alkyl, optionally substituted cycloalkyl, —NR$_2$, —SF$_5$, —OR, —CO$_2$R, —SR, —SOR, and —SO$_2$R;

D' is selected from the group consisting of a bond, optionally substituted alkyl, –O—, —S—, —NR—, —NRSO$_2$—, —SO$_2$NR—, —C(O)—, —C(O)O—, —C(O)NR—, —OC(O)—, —OC(O)NR—, —NRSO$_2$—, —NRC(O)—, —NRSO$_2$NR—, —NRC(O)O—, —NRCONR—, and —NRC(NR)NR—;

E' is selected from the group consisting of a bond, an optionally substituted C$_1$-C$_6$ alkyl, optionally substituted C$_2$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl.

7. The compound of claim 6, wherein R$^9$ is halogen, nitrile, a C$_1$-C$_6$ alkyl, or O-C$_1$-C$_6$ alkyl.

8. The compound of claim 6, wherein:
(a) n is 1; and/or
(b) le is pyridine; and/or
(c) Z is S; and/or
(d) R$^4$ is H.

9. The compound of claim 6, wherein R$^2$ and R$^3$ together are a cyclopropyl, cyclopentyl, cyclohexene, or a perdeuterated cycloalkyl ring.

10. A compound selected from Table I and depicted below, or a stereoisomer thereof, or a pharmaceutically acceptable salt thereof:

TABLE I
Compound
1
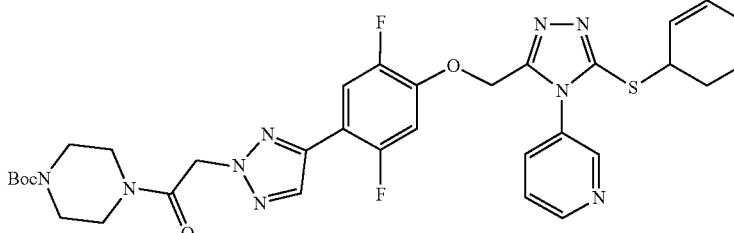
2
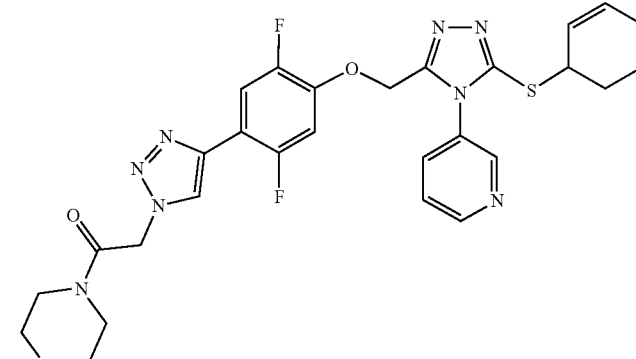
3
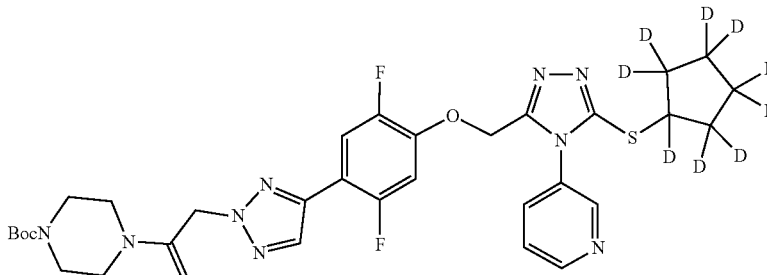
4
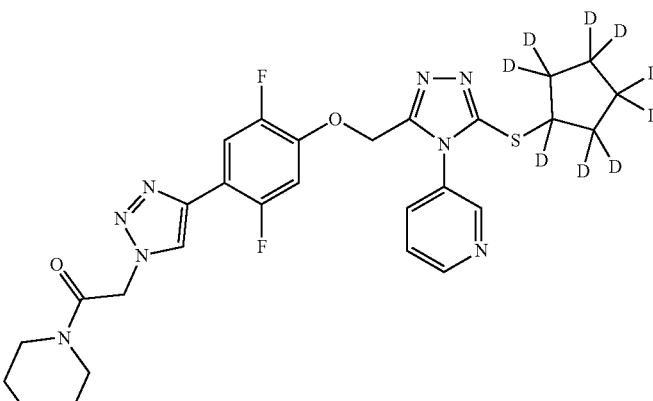

TABLE I-continued

| | Compound |
|---|---|
| 5 | (chemical structure) |
| 6 | (chemical structure) |
| 7 | (chemical structure) |
| 8 | (chemical structure) |
| 9 | (chemical structure) |

TABLE I-continued
| Compound |
|---|
| 10 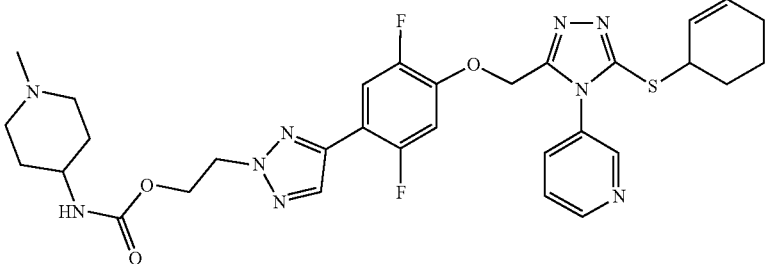 |
| 11 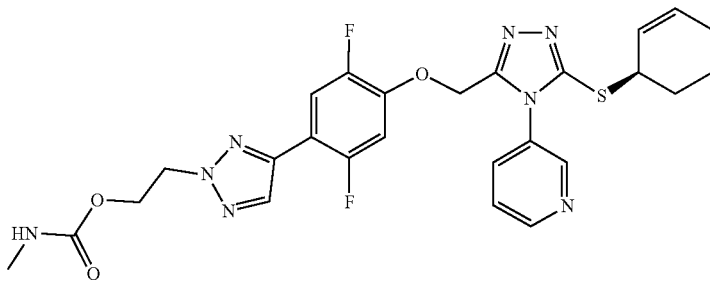 |
| 12 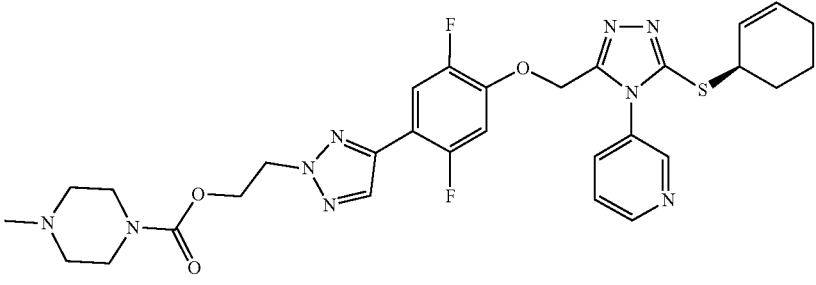 |
| 13 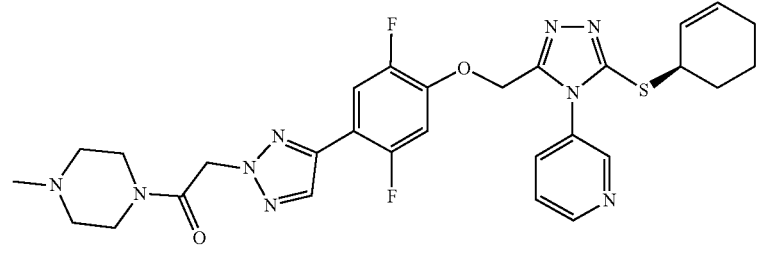 |
| 14 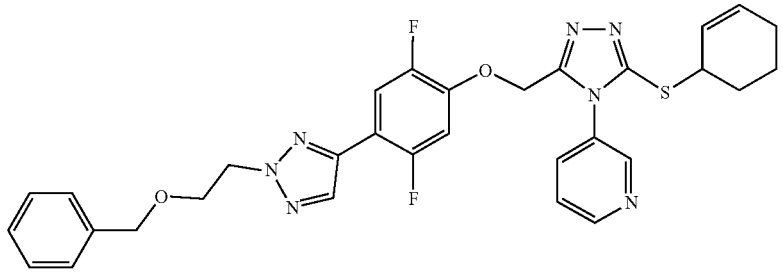 |

TABLE I-continued
Compound
15 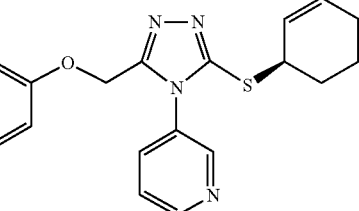
16 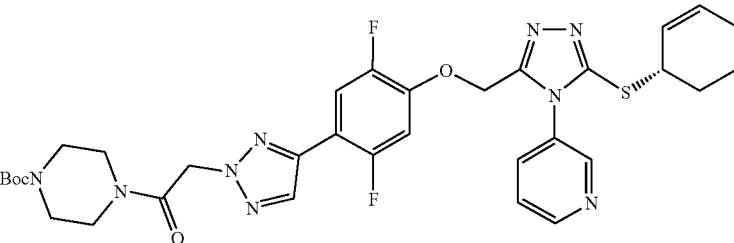
17 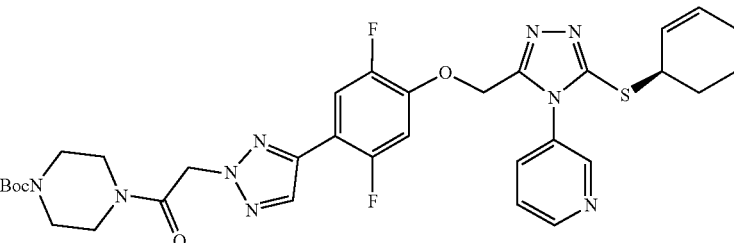
18 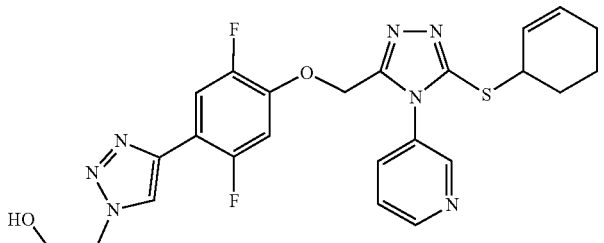
19 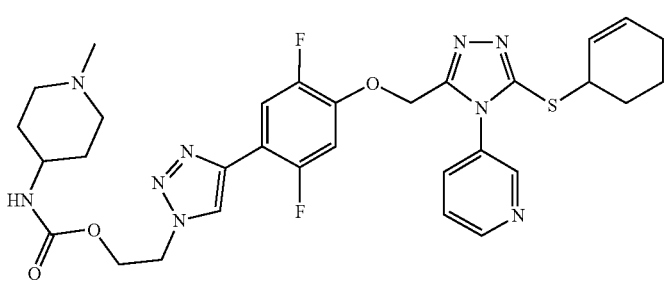
20 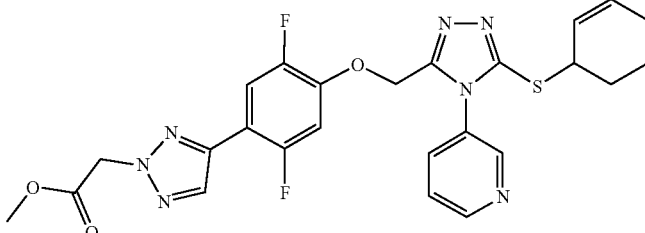

TABLE I-continued

Compound

21

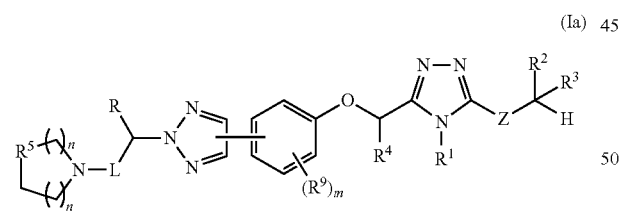

22

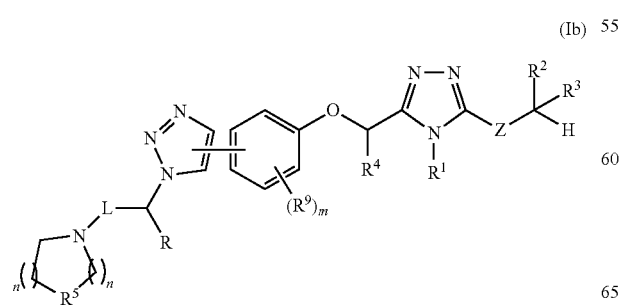

23

11. A pharmaceutical composition comprising a compound and at least one pharmaceutically acceptable excipient, wherein the compound is selected from the group consisting of:

(a) a compound having the structure of Formula (Ia) or Formula (Ib):

(Ia)

(Ib)

or a stereoisomer thereof, or a pharmaceutically acceptable salt thereof, wherein:

Z is O, $SO_{0-2}$, NR, or $C(R^7)_2$;

L is C(O) or $SO_{1-2}$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

m is 0, 1, 2, 3, or 4;

each n is independently 0, 1, 2, 3, or 4;

$R^5$ is $C(R^6)_2$, $NR^8$, $SO_{0-2}$, or O;

R is independently selected from the group consisting of H, optionally substituted alkyl, and optionally substituted cycloalkyl;

$R^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —$N(R^8)_2$; —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)

O-(optionally substituted aryl); —C(O)(NR)-(optionally substituted aryl); —SO$_{0-2}$-(optionally substituted aryl); —C(O)-(optionally substituted heterocyclic); —C(O)O-(optionally substituted heterocyclic); —C(O)(NR)-(optionally substituted heterocyclic); and —SO$_{0-2}$-(optionally substituted heterocyclic);

R$^7$ is independently selected from the group consisting of H, halogen, optionally substituted alkyl, optionally substituted cycloalkyl, —OR, and —N(R)$_2$, R$^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —SO$_{0-2}$-(optionally substituted alkyl); —C(O)-(optionally substituted cycloalkyl); —C(O)O-(optionally substituted cycloalkyl); —C(O)(NR)-(optionally substituted cycloalkyl); —SO$_{0-2}$-(optionally substituted cycloalkyl); —C(O)-(optionally substituted aryl); —C(O)O-(optionally substituted aryl); —C(O)(NR)-(optionally substituted aryl); —SO$_{0-2}$-(optionally substituted aryl); —C(O)-(optionally substituted heterocyclic); —C(O)O-(optionally substituted heterocyclic); —C(O)(NR)-(optionally substituted heterocyclic); and —SO$_{0-2}$-(optionally substituted heterocyclic); or two R$^8$, together with the nitrogen atom to which they are attached, form an optionally substituted heterocyclic ring; and R$^9$ is independently selected from the group consisting of halogen, nitrile, optionally substituted alkyl, optionally substituted cycloalkyl, —NR$_2$, —SF$_5$, —OR, —CO$_2$R, —SR, —SOR, and —SO$_2$R;

(b) a compound having the structure of Formula (IIa) or Formula (IIb):

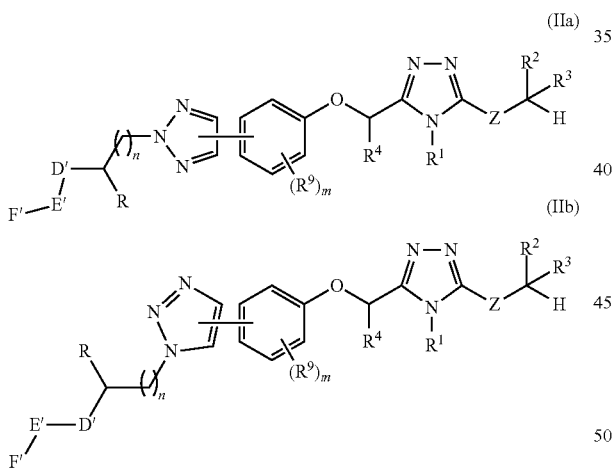

or a stereoisomer thereof, or a pharmaceutically acceptable salt thereof, wherein:

Z is O, SO$_{0-2}$, NR, or C(R$^7$)$_2$;

R$^2$ and R$^3$ are independently an optionally substituted C$_{1-9}$ cyclic, C$_{3-9}$ heterocyclic, or halogen, or R$^2$ and R$^3$ together form an optionally substituted C$_{3-9}$ cyclic or 3- to 9-membered heterocyclic ring;

R$^1$ is optionally substituted phenyl, optionally substituted 5- or 6-membered heteroaryl, or optionally substituted non-aromatic heterocyclic;

R$^4$ is H, C(R$^7$)$_3$, aryl, or heteroaryl;

R is independently selected from the group consisting of H, optionally substituted alkyl, and optionally substituted cycloalkyl;

R$^7$ is independently selected from the group consisting of H, halogen, optionally substituted alkyl, optionally substituted cycloalkyl, —OR, and —N(R)$_2$;

m is 0, 1, 2, 3, or 4;

n is 1, 2, 3, or 4;

R$^9$ is independently selected from the group consisting of halogen, nitrile, optionally substituted alkyl, optionally substituted cycloalkyl, —NR$_2$, —SF$_5$, —OR, —CO$_2$R, —SR, —SOR, and —SO$_2$R;

D' is selected from the group consisting of a bond, optionally substituted alkyl, –O—, —S—, —NR—, —NRSO$_2$—, —SO$_2$NR—, —C(O)—, —C(O)O—, —C(O)NR—, —OC(O)—, —OC(O)NR—, —NRSO$_2$—, —NRC(O)—, —NRSO$_2$NR—, —NRC(O)O—, —NRCONR—, and —NRC(NR)NR—;

E' is selected from the group consisting of a bond, an optionally substituted C$_1$-C$_6$ alkyl, optionally substituted C$_2$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl; and (c) a compound selected from Table I and depicted below, or a stereoisomer thereof, or a pharmaceutically acceptable salt thereof:

TABLE I

| Compound |
|---|
| 1 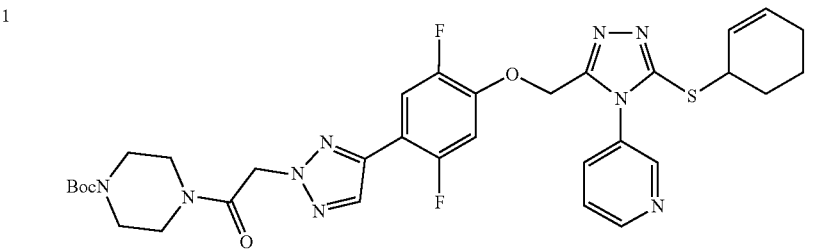 |

TABLE I-continued
| Compound |
|---|
| 2 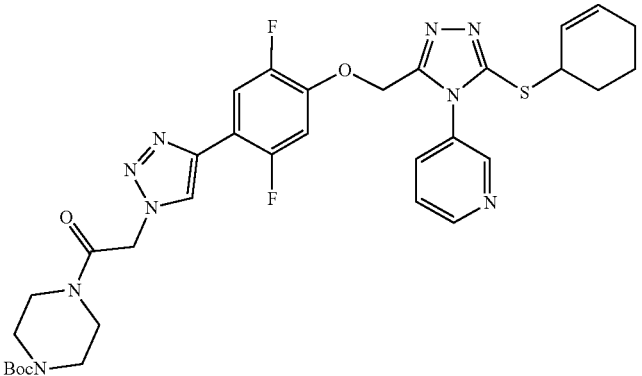 |
| 3 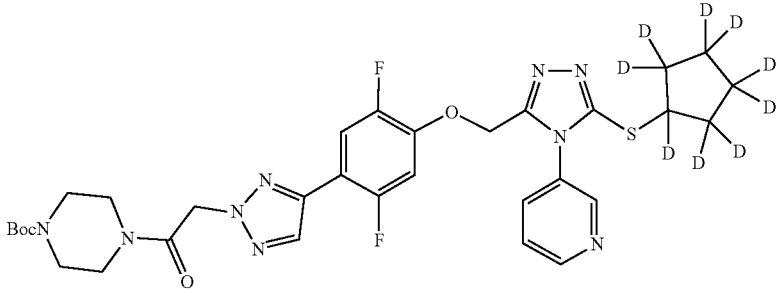 |
| 4 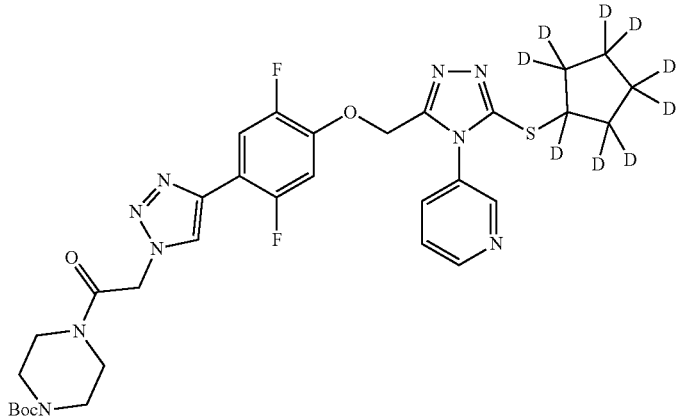 [SMILES: [2H]C1([2H])C([2H])([2H])C([2H])([2H])C([2H])(Sc2nnc(COc3cc(F)c(-c4cn(CC(=O)N5CCN(C(=O)OC(C)(C)C)CC5)nn4)cc3F)n2-c2cccnc2)C1([2H])[2H]] |
| 5 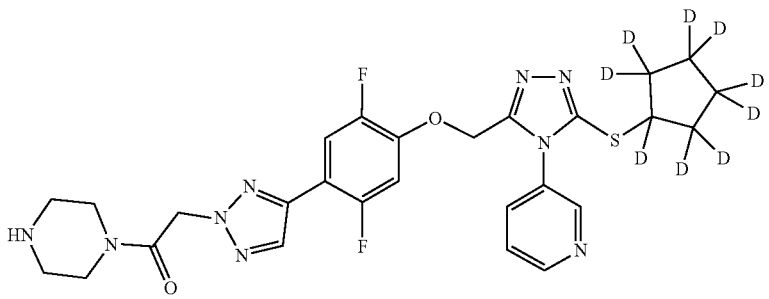 |

TABLE I-continued

| Compound |
|---|
| 6 (structure) |
| 7 (structure) |
| 8 (structure) |
| 9 (structure) |
| 10 (structure) |

TABLE I-continued
Compound
11 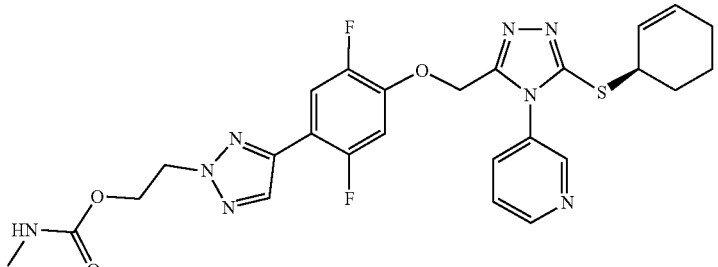
12 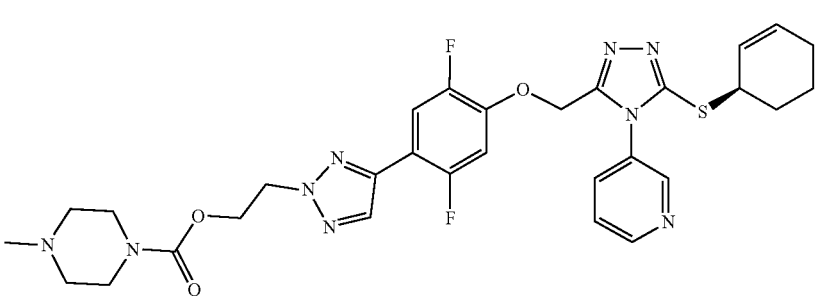
13 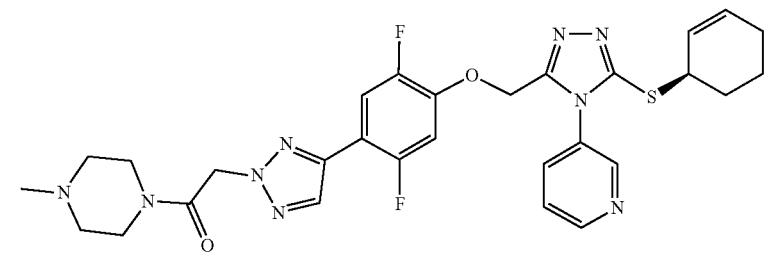
14 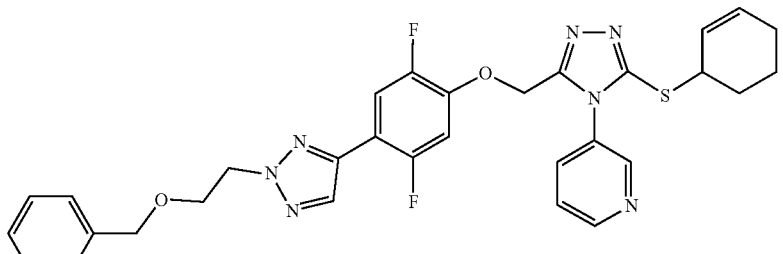
15 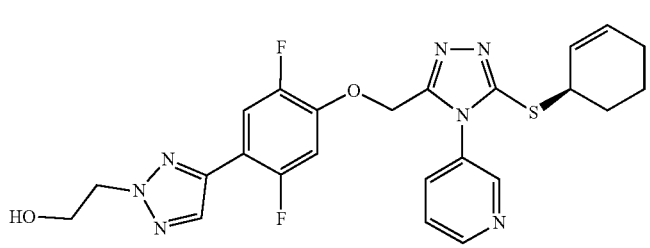
16 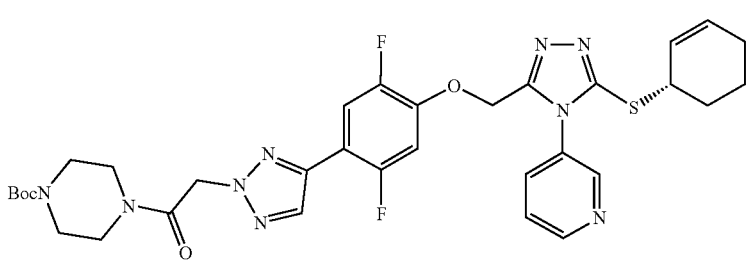

TABLE I-continued
Compound
17 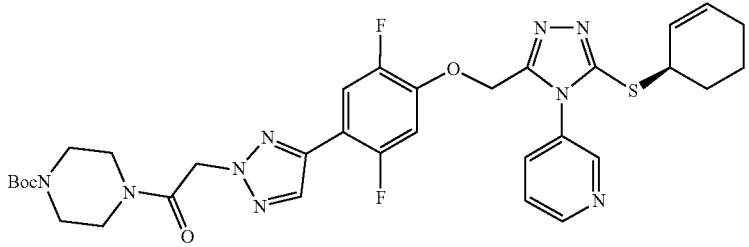
18 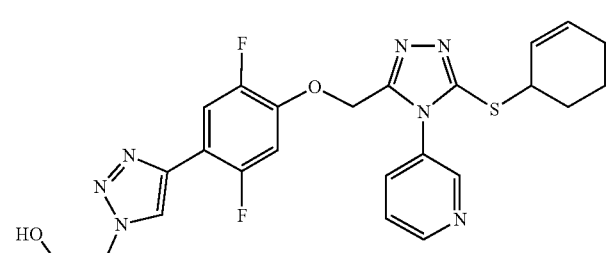
19 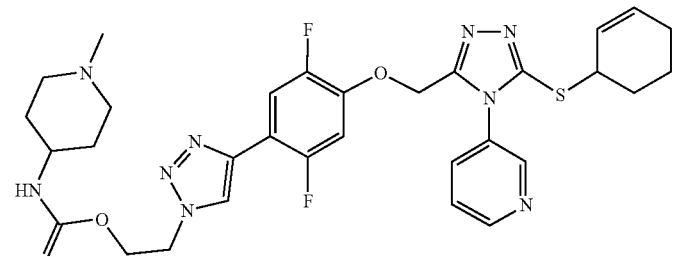
20 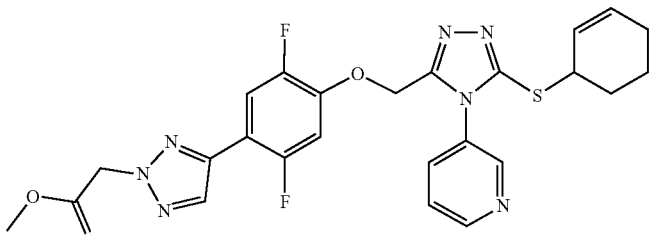
21 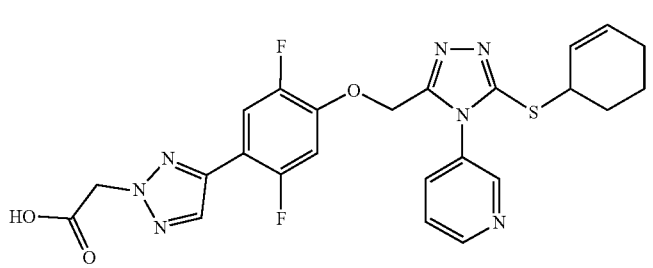
22 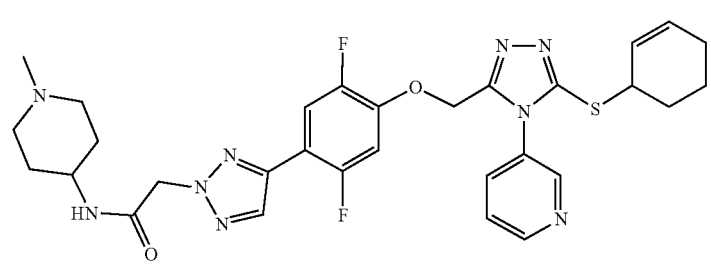

TABLE I-continued

| Compound |
|---|
| 23 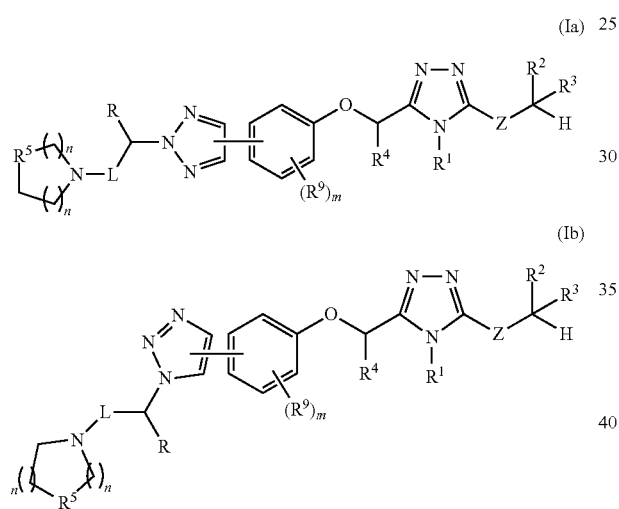 |

12. A method of inhibiting and/or modulating p97 in a subject, comprising administering to the subject a therapeutically effective amount of a compound selected from the group consisting of:

(a) a compound having the structure of Formula (Ia) or Formula (Ib):

(Ia)

(Ib)

or a stereoisomer thereof, or a pharmaceutically acceptable salt thereof, wherein:

Z is O, $SO_{0-2}$, NR, or $C(R^7)_2$;

L is C(O) or $SO_{1-2}$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

m is 0, 1, 2, 3, or 4;

each n is independently 0, 1, 2, 3, or 4;

$R^5$ is $C(R^6)_2$, $NR^8$, $SO_{0-2}$, or O;

R is independently selected from the group consisting of H, optionally substituted alkyl, and optionally substituted cycloalkyl;

$R^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —$N(R^8)_2$; —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic);

$R^7$ is independently selected from the group consisting of H, halogen, optionally substituted alkyl, optionally substituted cycloalkyl, —OR, and —$N(R)_2$;

$R^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic); or two $R^8$, together with the nitrogen atom to which they are attached, form an optionally substituted heterocyclic ring; and $R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$;

(b) a compound having the structure of Formula (IIa) or Formula (IIb):

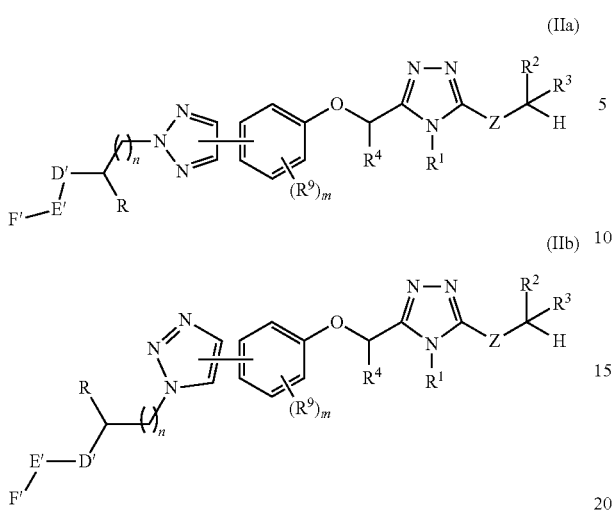

or a stereoisomer thereof, or a pharmaceutically acceptable salt thereof, wherein:

Z is O, $SO_{0-2}$, NR, or $C(R^7)_2$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

R is independently selected from the group consisting of H, optionally substituted alkyl, and optionally substituted cycloalkyl;

$R^7$ is independently selected from the group consisting of H, halogen, optionally substituted alkyl, optionally substituted cycloalkyl, —OR, and —$N(R)_2$;

m is 0, 1, 2, 3, or 4;

n is 1, 2, 3, or 4;

$R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$;

D' is selected from the group consisting of a bond, optionally substituted alkyl, -O—, —S—, —NR—, —$NRSO_2$—, —$SO_2NR$—, —C(O)—, —C(O)O—, —C(O)NR—, —OC(O)—, —OC(O)NR—, —$NRSO_2$—, —NRC(O)—, —$NRSO_2NR$—, —NRC(O)O—, —NRCONR—, and —NRC(NR)NR—, E' is selected from the group consisting of a bond, an optionally substituted $C_1$-$C_6$ alkyl, optionally substituted $C_2$-$C_6$ alkenyl, and optionally substituted cycloalkyl, and F' is selected from the group consisting of H, an optionally substituted cycloalkyl, an optionally substituted non-aromatic heterocycle, an optionally substituted aryl, and an optionally substituted heteroaryl; and (c) a compound selected from Table I and depicted below, or a stereoisomer thereof, or a pharmaceutically acceptable salt thereof:

TABLE I

| Compound |
| --- |
| 1 |
| 2 |

TABLE I-continued

| Compound |
|---|
| 3 |
| 4 |
| 5 |
| 6 |

TABLE I-continued

| Compound |
|---|
| 7 (structure) |
| 8 (structure) |
| 9 (structure) |
| 10 (structure) |
| 11 (structure) |
| 12 (structure) |

TABLE I-continued
| Compound | |
|---|---|
| 13 | 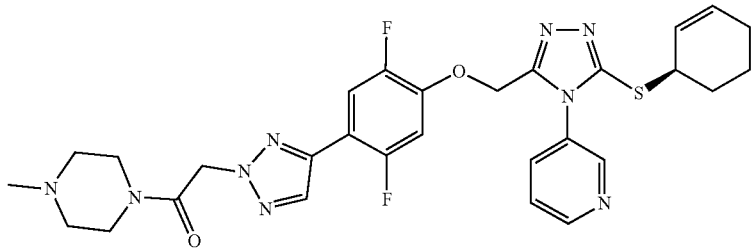 |
| 14 | 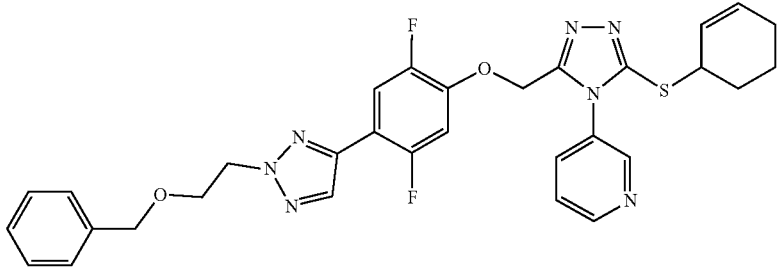 |
| 15 | 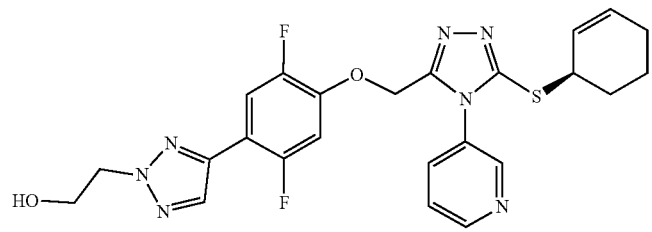 |
| 16 | 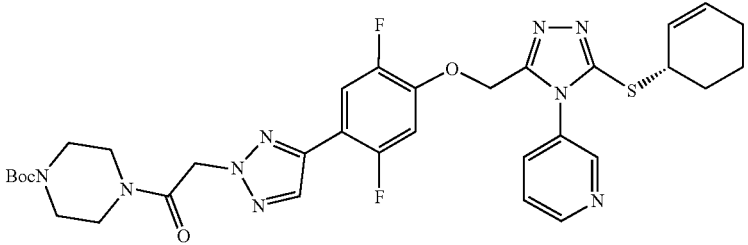 |
| 17 | 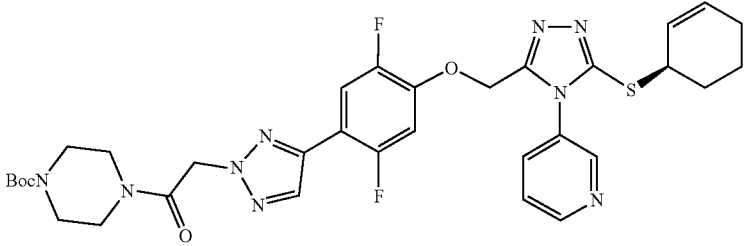 |
| 18 | 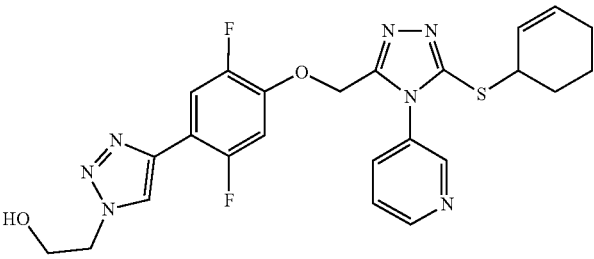 [SMILES: OCCn1cc(-c2cc(F)c(OCc3nnc(SC4C=CCCC4)n3-c3cccnc3)cc2F)nn1] |

TABLE I-continued

Compound

19 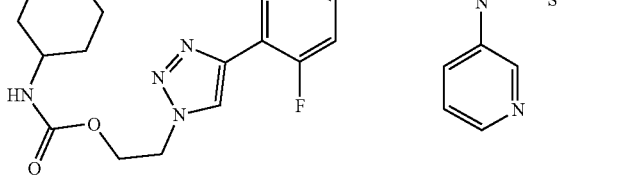

20 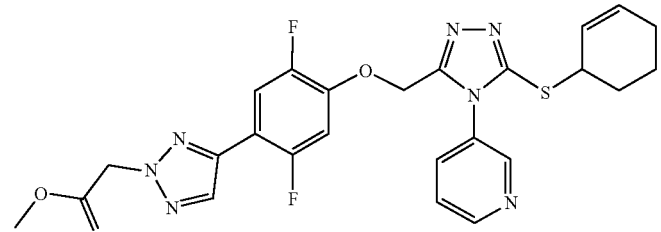

21 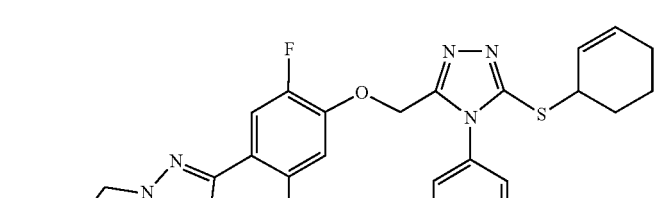

22 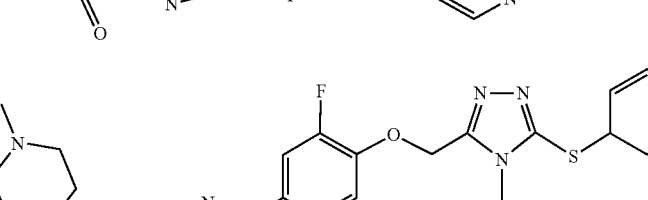

23 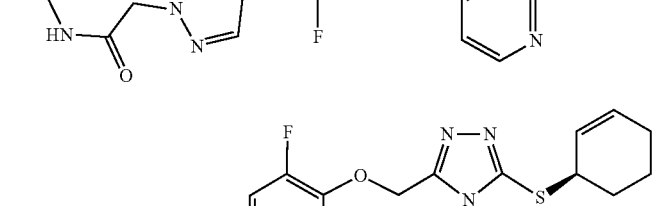

13. A method of treating cancer susceptible to treatment by p97 inhibition in a subject comprising administering to the subject a therapeutically effective amount of a compound, wherein:
  (a) the cancer is selected from the group consisting of a solid tumor, non-small cell lung carcinoma, multiple myeloma, and mantle cell lymphoma; and
  (b) the compound is selected from the group consisting of:
    (i) a compound having the structure of Formula (Ia) or Formula (Ib):

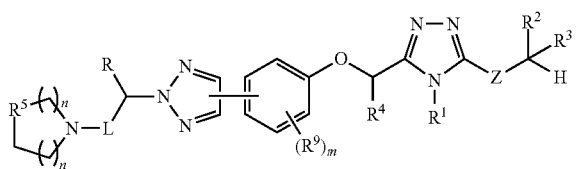

(Ia)

-continued

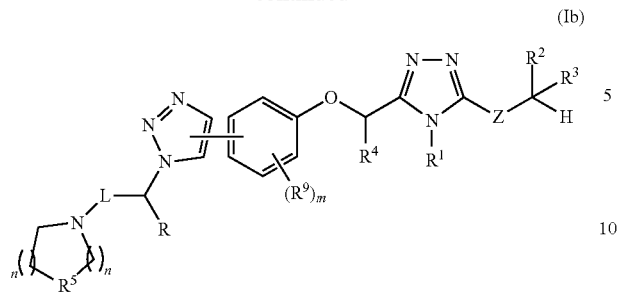
(Ib)

or a stereoisomer thereof, or a pharmaceutically acceptable salt thereof, wherein:

Z is O, $SO_{0-2}$, NR, or $C(R^7)_2$;

L is C(O) or $SO_{1-2}$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

m is 0, 1, 2, 3, or 4;

each n is independently 0, 1, 2, 3, or 4;

$R^5$ is $C(R^6)_2$, $NR^8$, $SO_{0-2}$ or O;

R is independently selected from the group consisting of H, optionally substituted alkyl, and optionally substituted cycloalkyl;

$R^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —$N(R^8)_2$; —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic);

$R^7$ is independently selected from the group consisting of H, halogen, optionally substituted alkyl, optionally substituted cycloalkyl, —OR, and —$N(R)_2$;

$R^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic); or two $R^8$, together with the nitrogen atom to which they are attached, form an optionally substituted heterocyclic ring; and $R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$;

(ii) a compound having the structure of Formula (IIa) or Formula (IIb):

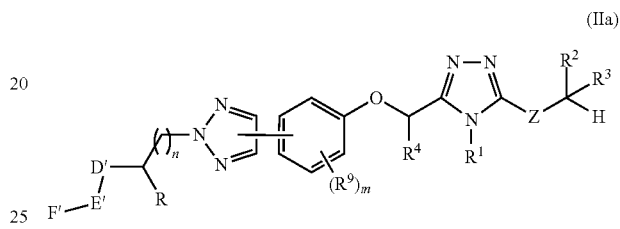
(IIa)

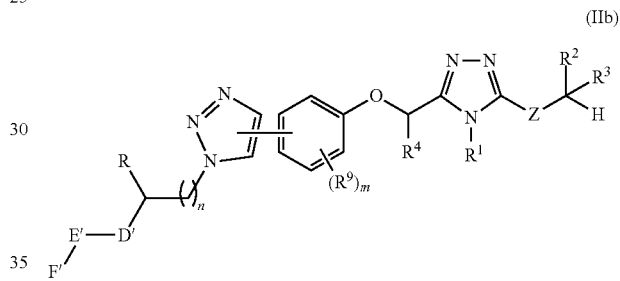
(IIb)

or a stereoisomer thereof, or a pharmaceutically acceptable salt thereof, wherein:

Z is O, $SO_{0-2}$, NR, or $C(R^7)_2$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

R is independently selected from the group consisting of H, optionally substituted alkyl, and optionally substituted cycloalkyl;

$R^7$ is independently selected from the group consisting of H, halogen, optionally substituted alkyl, optionally substituted cycloalkyl, —OR, and —$N(R)_2$;

m is 0, 1, 2, 3, or 4;

n is 1, 2, 3, or 4;

$R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$;

D' is selected from the group consisting of a bond, optionally substituted alkyl, -O—, —S—, —NR—, —$NRSO_2$—, —$SO_2NR$—, —C(O)—, —C(O)O—, —C(O)NR—, —OC(O)—, —OC(O)NR—, —$NRSO_2$—, —NRC(O)—, —$NRSO_2NR$—, —NRC(O)O—, —NRCONR—, and —NRC(NR)NR—, E' is selected from the group consisting of a bond, an optionally substituted $C_1$-$C_6$ alkyl, optionally substituted $C_2$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl; and (iii) a compound selected from Table I and depicted below, or a stereoisomer thereof, or a pharmaceutically acceptable salt thereof:

TABLE I

| | Compound |
|---|---|
| 1 | |
| 2 | |
| 3 | |
| 4 | |

TABLE I-continued

| | Compound |
|---|---|
| 5 | (chemical structure) |
| 6 | (chemical structure) |
| 7 | (chemical structure) |
| 8 | (chemical structure) |
| 9 | (chemical structure) |

TABLE I-continued
| Compound |
|---|
| 10 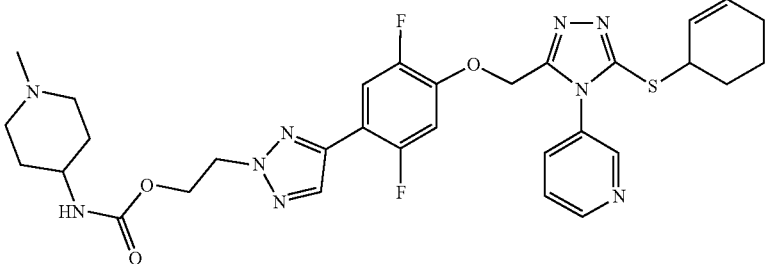 |
| 11 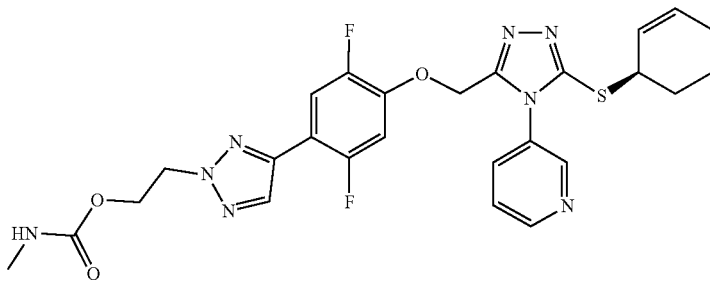 |
| 12 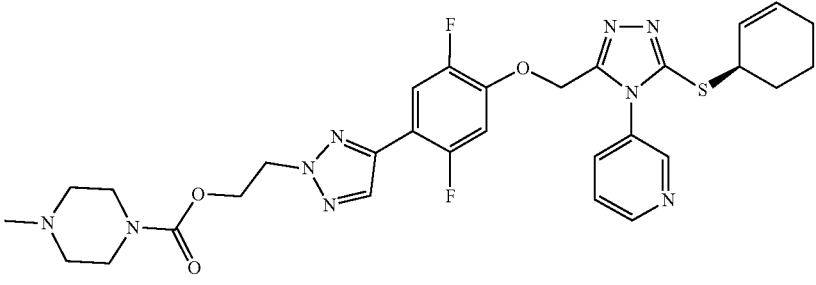 |
| 13 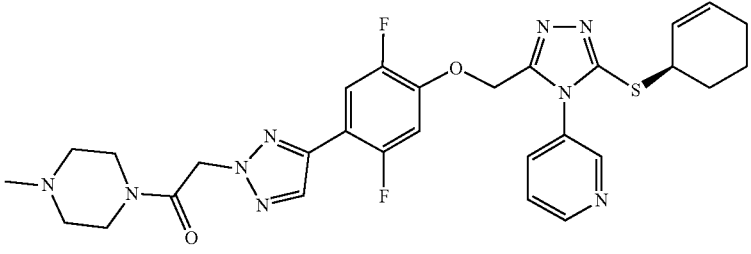 |
| 14 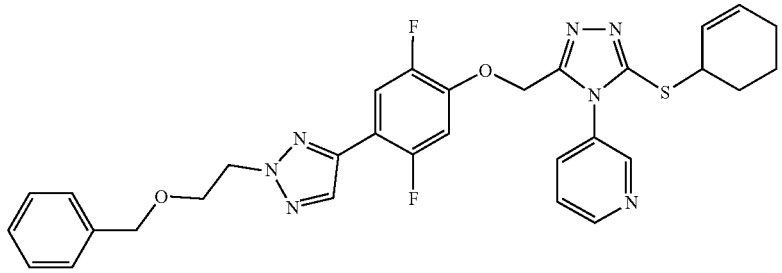 |

TABLE I-continued
Compound
15 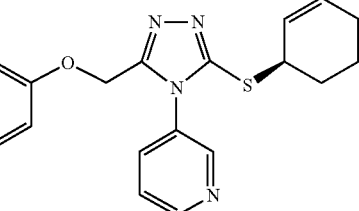
16 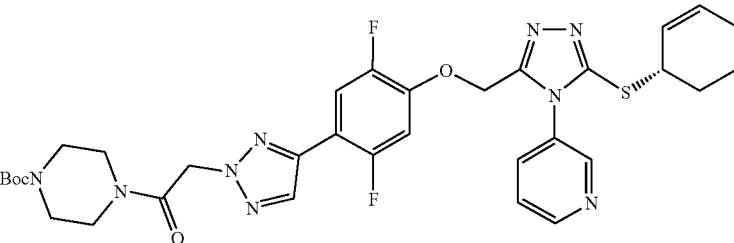
17 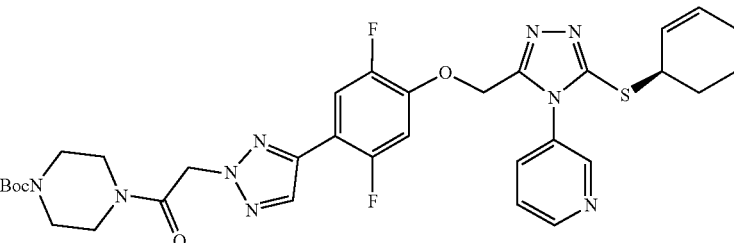
18 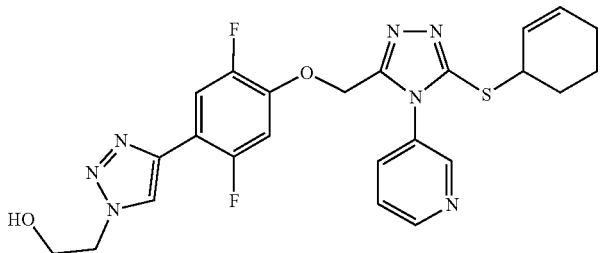
19 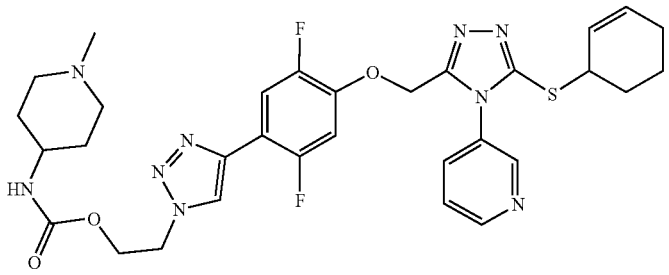
20 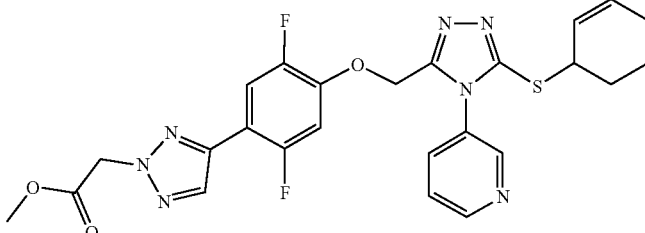

TABLE I-continued

Compound

21
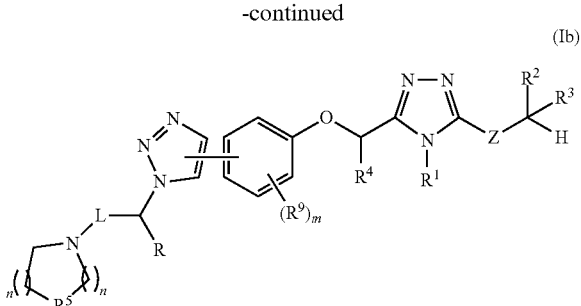

22

23

14. A method of treating a neurodegenerative disease susceptible to treatment by p97 inhibition in a subject, comprising administering to the subject a therapeutically effective amount of a compound, wherein:
   (a) the neurodegenerative disease is selected from the group consisting of inclusion body myopathy (IBM), Paget's disease of the bone (PDB), frontotemporal dementia (FTD) and amyotrophic lateral sclerosis (ALS), and
   (b) the compound is selected from the group consisting of:
      (i) a compound having the structure of Formula (Ia) or Formula (Ib):

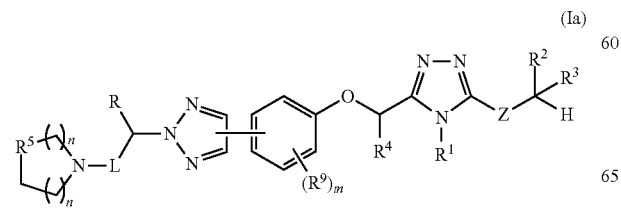

or a stereoisomer thereof, or a pharmaceutically acceptable salt thereof, wherein:
Z is O, $SO_{0-2}$, NR, or $C(R^7)_2$;
L is C(O) or $SO_{1-2}$;
$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;
$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

m is 0, 1, 2, 3, or 4;

each n is independently 0, 1, 2, 3, or 4;

$R^5$ is $C(R^6)_2$, $NR^8$, $SO_{0-2}$, or O;

R is independently selected from the group consisting of H, optionally substituted alkyl, and optionally substituted cycloalkyl;

$R^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —$N(R^8)_2$; —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic);

$R^7$ is independently selected from the group consisting of H, halogen, optionally substituted alkyl, optionally substituted cycloalkyl, —OR, and —$N(R)_2$;

$R^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —$SO_{0-2}$-(optionally substituted alkyl); —C(O)-(optionally substituted cycloalkyl); —C(O)O-(optionally substituted cycloalkyl); —C(O)(NR)-(optionally substituted cycloalkyl); —$SO_{0-2}$-(optionally substituted cycloalkyl); —C(O)-(optionally substituted aryl); —C(O)O-(optionally substituted aryl); —C(O)(NR)-(optionally substituted aryl); —$SO_{0-2}$-(optionally substituted aryl); —C(O)-(optionally substituted heterocyclic); —C(O)O-(optionally substituted heterocyclic); —C(O)(NR)-(optionally substituted heterocyclic); and —$SO_{0-2}$-(optionally substituted heterocyclic); or two $R^8$, together with the nitrogen atom to which they are attached, form an optionally substituted heterocyclic ring; and $R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$;

(ii) a compound having the structure of Formula (IIa) or Formula (IIb):

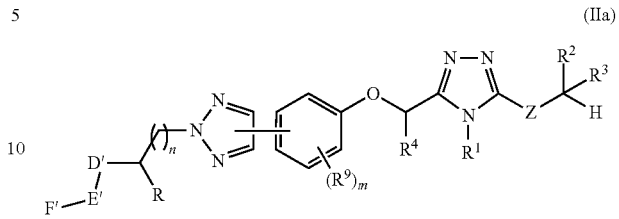

or a stereoisomer thereof, or a pharmaceutically acceptable salt thereof, wherein:

Z is O, $SO_{0-2}$, NR, or $C(R^7)_2$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_3$, aryl, or heteroaryl;

R is independently selected from the group consisting of H, optionally substituted alkyl, and optionally substituted cycloalkyl;

$R^7$ is independently selected from the group consisting of H, halogen, optionally substituted alkyl, optionally substituted cycloalkyl, —OR, and —$N(R)_2$;

m is 0, 1, 2, 3, or 4;

n is 1, 2, 3, or 4;

$R^9$ is independently selected from the group consisting of halogen, nitrile, optionally substituted alkyl, optionally substituted cycloalkyl, —$NR_2$, —$SF_5$, —OR, —$CO_2R$, —SR, —SOR, and —$SO_2R$;

D' is selected from the group consisting of a bond, optionally substituted alkyl, –O—, —S—, —NR—, —$NRSO_2$—, —$SO_2NR$—, —C(O)—, —C(O)O—, —C(O)NR—, —OC(O)—, —OC(O)NR—, —$NRSO_2$—, —NRC(O)—, —$NRSO_2NR$—, —NRC(O)O—, —NRCONR—, and —NRC(NR)NR—;

E' is selected from the group consisting of a bond, an optionally substituted $C_1$-$C_6$ alkyl, optionally substituted $C_2$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl; and (iii) a compound selected from Table I and depicted below, or a stereoisomer thereof, or a pharmaceutically acceptable salt thereof:

TABLE I

| | Compound |
|---|---|
| 1 | |
| 2 | |
| 3 | |
| 4 | |

TABLE I-continued

| | Compound |
|---|---|
| 5 | (structure) |
| 6 | (structure) |
| 7 | (structure) |
| 8 | (structure) |
| 9 | (structure) |

TABLE I-continued

Compound

10

11

12

13

14

TABLE I-continued
| Compound | |
|---|---|
| 15 | 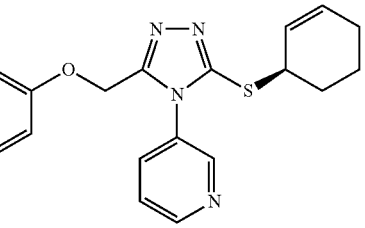 |
| 16 | 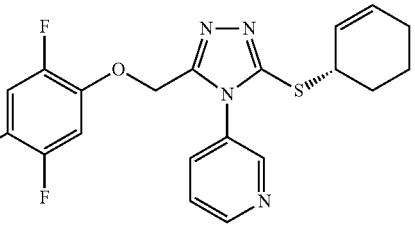 |
| 17 | 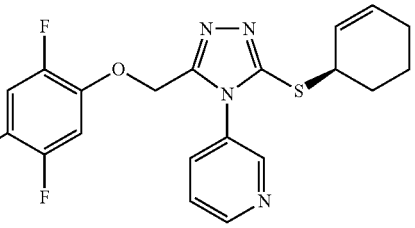 |
| 18 | 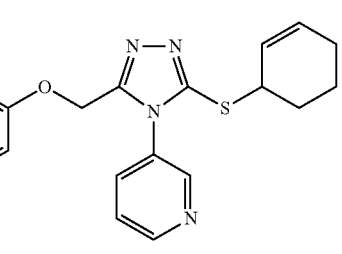 |
| 19 | 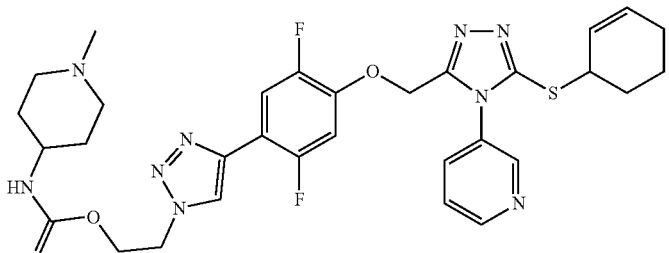 |
| 20 | 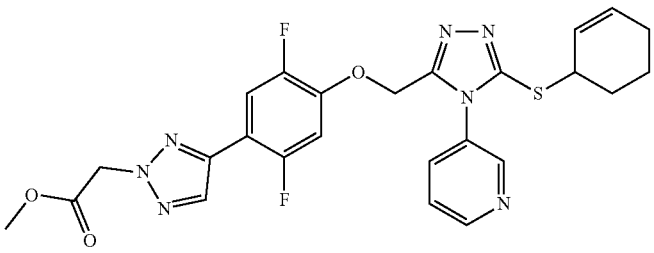 [SMILES: COC(=O)Cn1ncc(-c2cc(F)c(OCc3nnc(SC4C=CCCC4)n3-c3cccnc3)cc2F)n1] |

TABLE I-continued

Compound

21 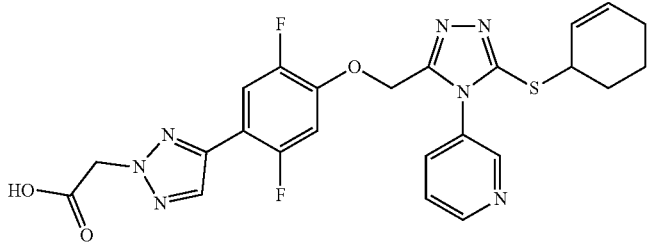 [SMILES: O=C(O)Cn1ncc(-c2cc(F)c(OCc3nnc(SC4C=CCCC4)n3-c3cccnc3)cc2F)n1]

22 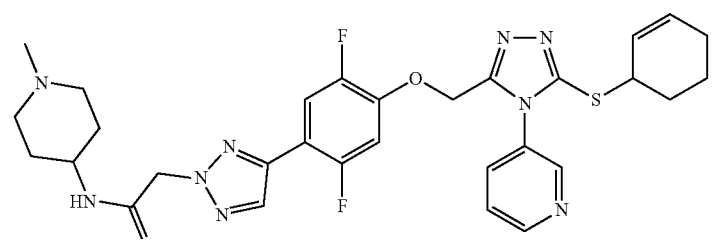

23 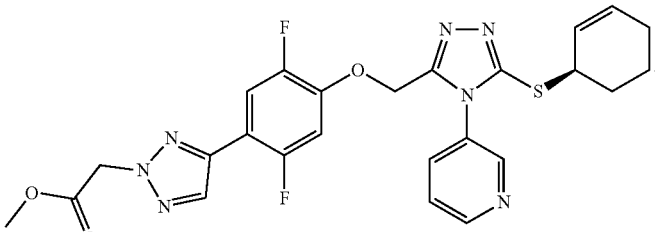

15. A method of treating a antibacterial and/or antiviral infection in a subject comprising administering to the subject a therapeutically effective amount of a compound, wherein:

(a) the antibacterial and/or antiviral infection is susceptible to treatment by modulation or inhibition of p97; and (b) the compound is selected from the group consisting of:
  (i) a compound having the structure of Formula (Ia) or Formula (Ib):

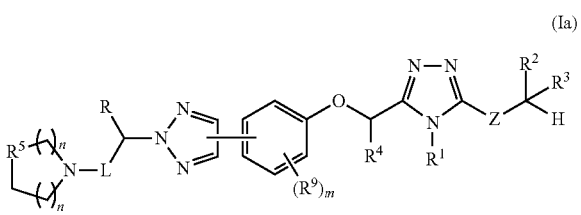

(Ia)

-continued

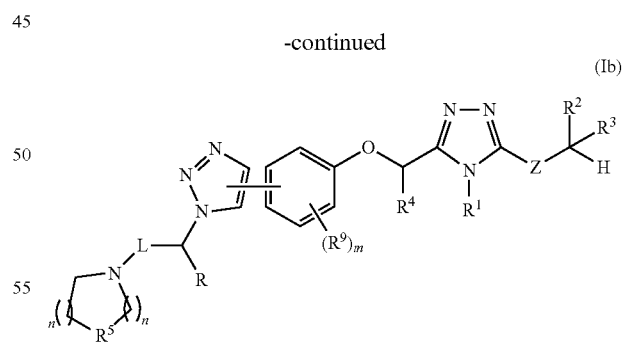

(Ib)

or a stereoisomer thereof, or a pharmaceutically acceptable salt thereof, wherein:

Z is O, $SO_{0-2}$, NR, or $C(R^7)_2$;

L is C(O) or $SO_{1-2}$;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

R$^1$ is optionally substituted phenyl, optionally substituted 5- or 6-membered heteroaryl, or optionally substituted non-aromatic heterocyclic;

R$^4$ is H, C(R$^7$)$_3$, aryl, or heteroaryl;

m is 0, 1, 2, 3, or 4;

each n is independently 0, 1, 2, 3, or 4;

R$^5$ is C(R$^6$)$_2$, NR$^8$, SO$_{0-2}$, or O;

R is independently selected from the group consisting of H, optionally substituted alkyl, and optionally substituted cycloalkyl;

R$^6$ is independently selected from the group consisting of H, halogen, nitrile, hydroxy, optionally substituted alkoxy, optionally substituted alkyl, optionally substituted cycloalkyl, optionally substituted aryl, optionally substituted heterocyclic, —N(R$^8$)$_2$; —C(O)-(optionally substituted alkyl); —C(O)O-(optionally substituted alkyl); —C(O)(NR)-(optionally substituted alkyl); —SO$_{0-2}$-(optionally substituted alkyl); —C(O)-(optionally substituted cycloalkyl); —C(O)O-(optionally substituted cycloalkyl); —C(O)(NR)-(optionally substituted cycloalkyl); —SO$_{0-2}$-(optionally substituted cycloalkyl); —C(O)-(optionally substituted aryl); —C(O)O-(optionally substituted aryl); —C(O)(NR)-(optionally substituted aryl); —SO$_{0-2}$-(optionally substituted aryl); —C(O)-(optionally substituted heterocyclic); —C(O)O-(optionally substituted heterocyclic); —C(O)(NR)-(optionally substituted heterocyclic); and —SO$_{0-2}$-(optionally substituted heterocyclic);

R$^7$ is independently selected from the group consisting of H, halogen, optionally substituted alkyl, optionally substituted cycloalkyl, —OR, and —N(R)$_2$;

R$^8$ is independently selected from the group consisting of H, optionally substituted alkyl, optionally substituted cycloalkyl, optionally substituted aryl, optionally substituted heterocyclic, —C(O)-(optionally substituted alkyl); —C(O)O-(optionally substituted alkyl); —C(O)(NR)-(optionally substituted alkyl); —SO$_{0-2}$-(optionally substituted alkyl); —C(O)-(optionally substituted cycloalkyl); —C(O)O-(optionally substituted cycloalkyl); —C(O)(NR)-(optionally substituted cycloalkyl); —SO$_{0-2}$-(optionally substituted cycloalkyl); —C(O)-(optionally substituted aryl); —C(O)O-(optionally substituted aryl); —C(O)(NR)-(optionally substituted aryl); —SO$_{0-2}$-(optionally substituted aryl); —C(O)-(optionally substituted heterocyclic); —C(O)O-(optionally substituted heterocyclic); —C(O)(NR)-(optionally substituted heterocyclic); and —SO$_{0-2}$-(optionally substituted heterocyclic); or two R$^8$, together with the nitrogen atom to which they are attached, form an optionally substituted heterocyclic ring; and R$^9$ is independently selected from the group consisting of halogen, nitrile, optionally substituted alkyl, optionally substituted cycloalkyl, —NR$_2$, —SF$_5$, —OR, —CO$_2$R, —SR, —SOR, and —SO$_2$R;

(ii) a compound having the structure of Formula (IIa) or Formula (IIb):

(IIa)

(IIb)

or a stereoisomer thereof, or a pharmaceutically acceptable salt thereof, wherein:

Z is O, SO$_{0-2}$, NR, or C(R$^7$)$_2$;

R$^2$ and R$^3$ are independently an optionally substituted C$_{1-9}$ cyclic, C$_{3-9}$ heterocyclic, or halogen, or R$^2$ and R$^3$ together form an optionally substituted C$_{3-9}$ cyclic or 3- to 9-membered heterocyclic ring;

R$^1$ is optionally substituted phenyl, optionally substituted 5- or 6-membered heteroaryl, or optionally substituted non-aromatic heterocyclic;

R$^4$ is H, C(R$^7$)$_3$, aryl, or heteroaryl;

R is independently selected from the group consisting of H, optionally substituted alkyl, and optionally substituted cycloalkyl;

R$^7$ is independently selected from the group consisting of H, halogen, optionally substituted alkyl, optionally substituted cycloalkyl, —OR, and —N(R)$_2$;

m is 0, 1, 2, 3, or 4;

n is 1, 2, 3, or 4;

R$^9$ is independently selected from the group consisting of halogen, nitrile, optionally substituted alkyl, optionally substituted cycloalkyl, —NR$_2$, —SF$_5$, —OR, —CO$_2$R, —SR, —SOR, and —SO$_2$R;

D' is selected from the group consisting of a bond, optionally substituted alkyl, —O—, —S—, —NR—, —NRSO$_2$—, —SO$_2$NR—, —C(O)—, —C(O)O—, —C(O)NR—, —OC(O)—, —OC(O)NR—, —NRSO$_2$—, —NRC(O)—, —NRSO$_2$NR—, —NRC(O)O—, —NRCONR—, and —NRC(NR)NR—;

E' is selected from the group consisting of a bond, an optionally substituted C$_1$-C$_6$ alkyl, optionally substituted C$_2$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl; and (iii) a compound selected from Table I and depicted below, or a stereoisomer thereof, or a pharmaceutically acceptable salt thereof:

TABLE I
| Compound |
|---|
| 1 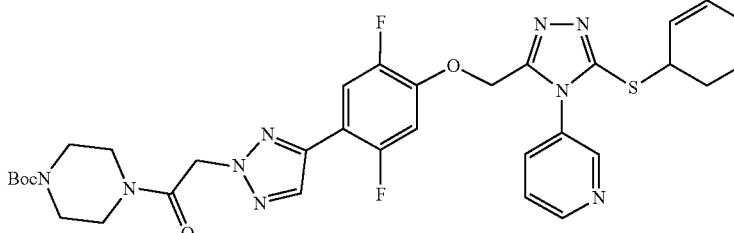 |
| 2 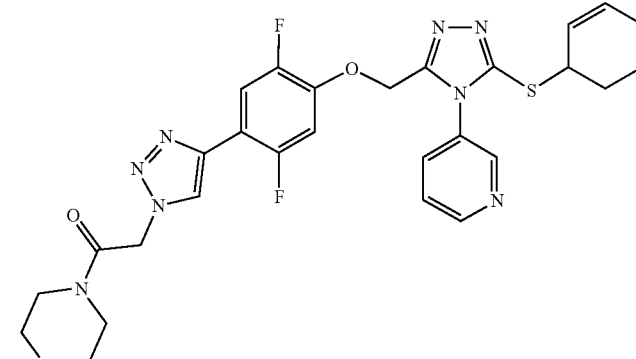 |
| 3 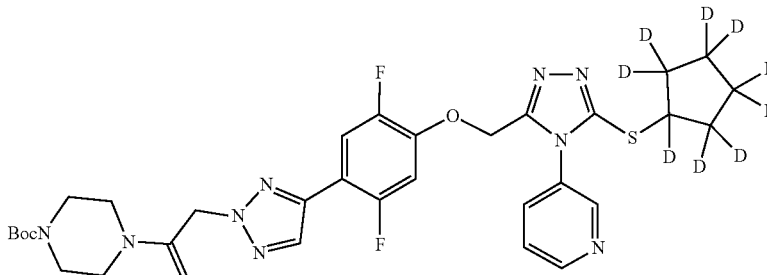 |
| 4 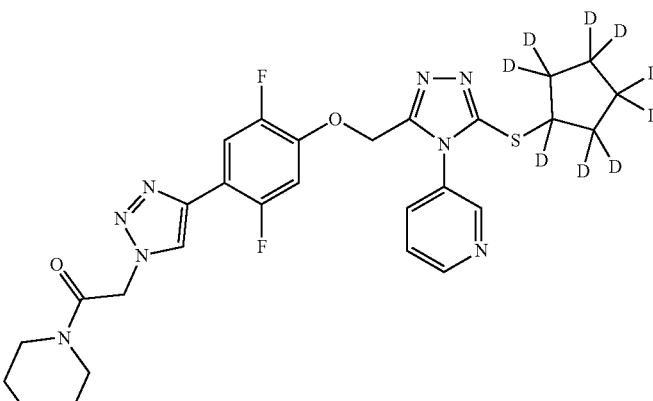 |

TABLE I-continued

| | Compound |
|---|---|
| 5 | (structure) |
| 6 | (structure) |
| 7 | (structure) |
| 8 | (structure) |
| 9 | (structure) |

TABLE I-continued
| Compound |
|---|
| 10 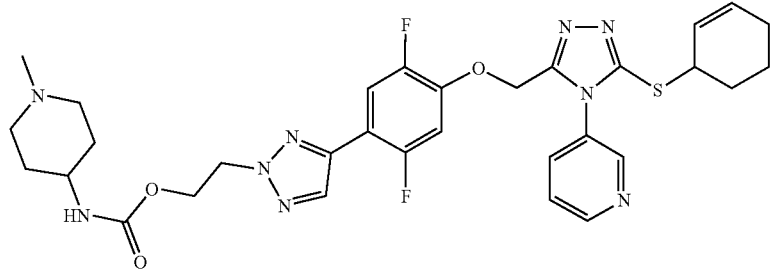 |
| 11 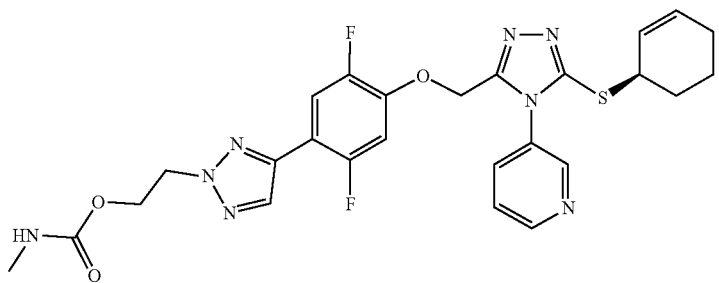 |
| 12 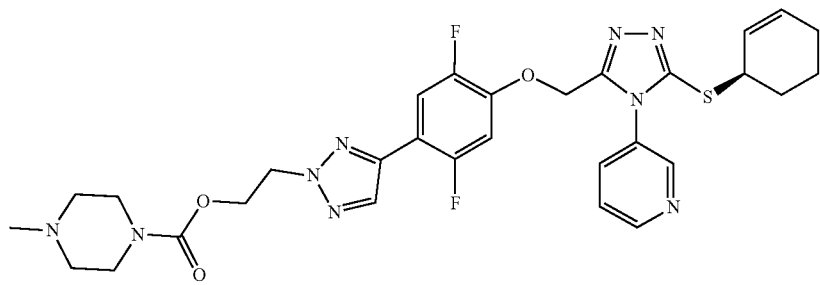 |
| 13 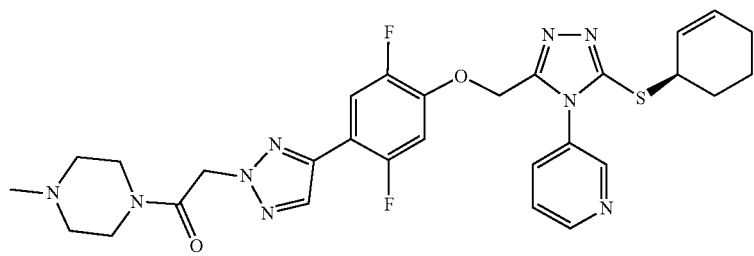 |
| 14 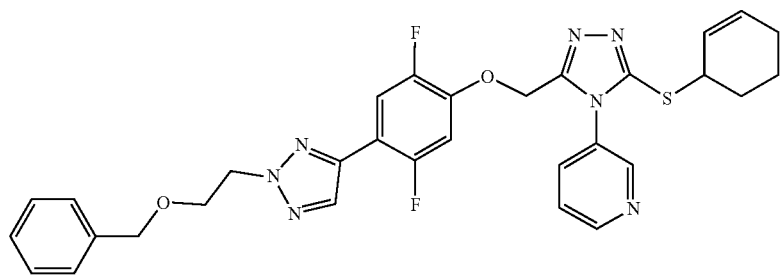 |

TABLE I-continued
| Compound | |
|---|---|
| 15 | 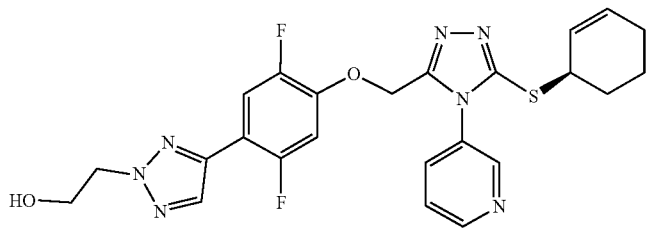 |
| 16 | 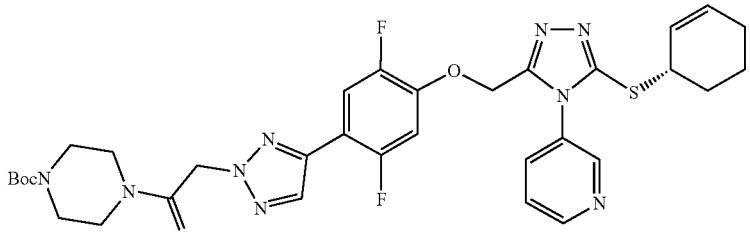 |
| 17 | 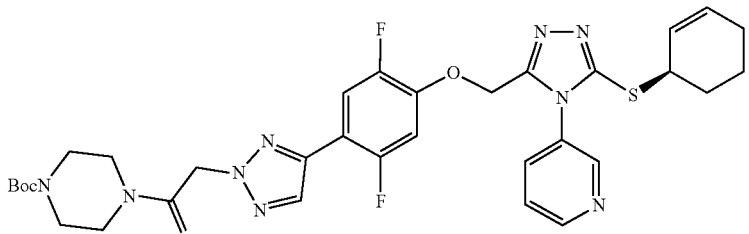 |
| 18 | 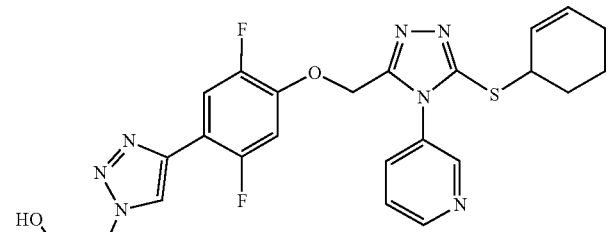 |
| 19 | 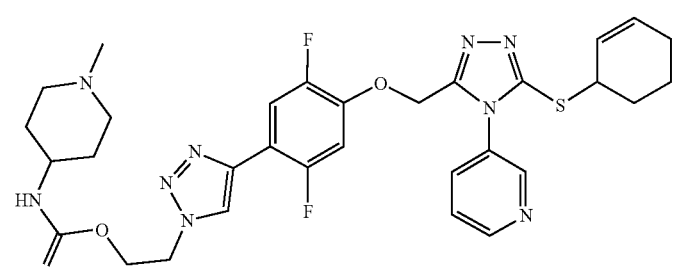 |
| 20 | 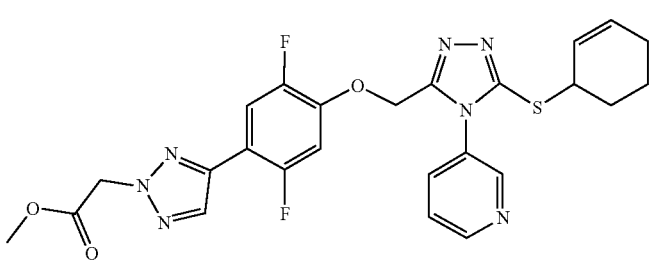 |

TABLE I-continued
| Compound | |
|---|---|
| 21 | 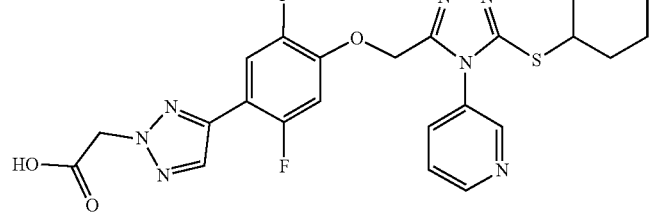 |
| 22 | 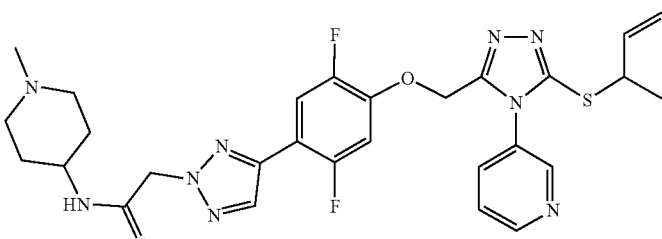 |
| 23 | 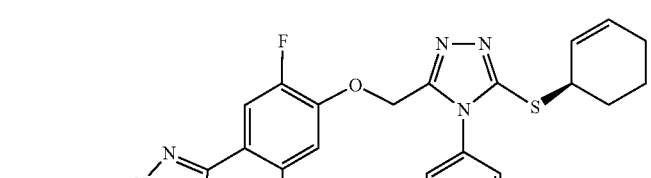 |
* * * * *

UNITED STATES PATENT AND TRADEMARK OFFICE
CERTIFICATE OF CORRECTION

| | |
|---|---|
| PATENT NO. | : 11,718,600 B2 |
| APPLICATION NO. | : 17/046255 |
| DATED | : August 8, 2023 |
| INVENTOR(S) | : Huryn et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 326 days.

Signed and Sealed this
Twelfth Day of November, 2024

*Katherine Kelly Vidal*

Katherine Kelly Vidal
*Director of the United States Patent and Trademark Office*